(12) United States Patent
Huang et al.

(10) Patent No.: US 7,304,208 B2
(45) Date of Patent: Dec. 4, 2007

(54) EXPRESSION OF HUMAN SERUM ALBUMIN (HSA) IN MONOCOT SEEDS

(75) Inventors: Ning Huang, Davis, CA (US); Raymond L. Rodriquez, Davis, CA (US); Frank E. Hagie, Sacramento, CA (US); David M. Stalker, Woodland, CA (US)

(73) Assignee: Ventria Bioscience, Sacramento, CA (US)

( * ) Notice: Subject to any disclaimer, the term of this patent is extended or adjusted under 35 U.S.C. 154(b) by 468 days.

(21) Appl. No.: 10/411,395

(22) Filed: Apr. 11, 2003

(65) Prior Publication Data

US 2003/0221223 A1    Nov. 27, 2003

Related U.S. Application Data

(63) Continuation-in-part of application No. 10/077,381, filed on Feb. 14, 2002, now Pat. No. 6,991,824, and a continuation-in-part of application No. 09/847,232, filed on May 2, 2001, now abandoned.

(60) Provisional application No. 60/269,199, filed on Feb. 14, 2001, provisional application No. 60/266,929, filed on Feb. 6, 2001, provisional application No. 60/201,182, filed on May 2, 2000.

(51) Int. Cl.
  C12N 15/82 (2006.01)
  A01H 5/00 (2006.01)
  C07H 21/04 (2006.01)

(52) U.S. Cl. ...................................... 800/288; 800/287
(58) Field of Classification Search ...................... None
  See application file for complete search history.

(56) References Cited

U.S. PATENT DOCUMENTS

| | | | |
|---|---|---|---|
| 5,639,947 A | | 6/1997 | Hiatt et al. |
| 5,763,748 A | * | 6/1998 | Sijmons et al. ............. 800/298 |
| 5,767,363 A | | 6/1998 | De Silva et al. |
| 5,959,177 A | | 9/1999 | Hein et al. |
| 5,994,628 A | * | 11/1999 | Rodriguez ................... 800/298 |
| 6,303,341 B1 | | 10/2001 | Hiatt et al. |
| 6,344,600 B1 | | 2/2002 | Merot et al. |
| 6,417,429 B1 | | 7/2002 | Hein et al. |
| 2002/0046418 A1 | | 4/2002 | Hooker et al. |
| 2002/0078472 A1 | * | 6/2002 | Christou et al. ............ 800/278 |
| 2002/0174453 A1 | | 11/2002 | Daniell et al. |

FOREIGN PATENT DOCUMENTS

| | | | |
|---|---|---|---|
| WO | WO 99/16890 | * | 4/1999 |
| WO | WO 02/064750 A2 | | 8/2002 |

OTHER PUBLICATIONS

Daniell et al., Medical molecular farming: production of antibodies, biopharmaceuticals and edible vaccines in plants, Trends in Plant Science vol. 6, No. 5, May 2001, pp. 219-226.
"Expression and Purification of Functional Human α-1 Antitrypsin from Cultured Plant Cells", Huang et al. *Biotechnol. Prog.*, 17, 2001, pp. 126-133.
"Medical molecular farming: production of antibodies, biopharmaceuticals and edible vaccines in plants", Daniell, *TRENDS in Plant Science*, 6(5), 2001, pp. 219-226.
"The production of recombinant proteins in transgenic barley grains", Horvath et al., *PNAS*, 97(4), 2000, pp. 1914-1919.
Production of correctly processed human serum albumin in transgenic plants, Sijmons et al., *Bio/Technology*, 8, 1990, pp. 217-221.
"Targeted expression of human serum albumin to potato tubers", Farran et al., *Transgenic Research*, 11, 2002, pp. 337-346.
"A chloroplast transgenic approach to hyper-express and purify Human Serum Albumin, a protein highly susceptible to proteolytic degradation", San Millian et al., *Plant Biotechnology Journal*, 1, 2003, pp. 71-79.

* cited by examiner

*Primary Examiner*—Anne Kubelik
*Assistant Examiner*—Cathy Kingdon Worley
(74) *Attorney, Agent, or Firm*—Arent Fox LLP

(57) ABSTRACT

A method of producing human serum albumin (HSA) in monocot plant seeds, by transforming a monocot plant cell with a chimeric gene containing a promoter from the gene of a maturation-specific monocot plant storage protein, a first DNA sequence operably linked to the promoter and encoding a signal sequence, and a second DNA sequence linked in translation frame with the first DNA sequence and encoding HSA, where the first DNA sequence and the second DNA sequence together encode a fusion protein containing an N-terminal signal sequence and the HSA; growing a monocot plant from the transformed monocot plant cell for a time sufficient to produce seeds containing the HSA; and harvesting the seeds from the plant.

2 Claims, 11 Drawing Sheets

Figure 1. Restriction maps of plasmids (pAPI 398), (pAPI 417) and (pAPI 327); containing the codon-optomized human fibrinogen genes for α, β and γ genes respectively each under the control of the rice glutelin promoter.
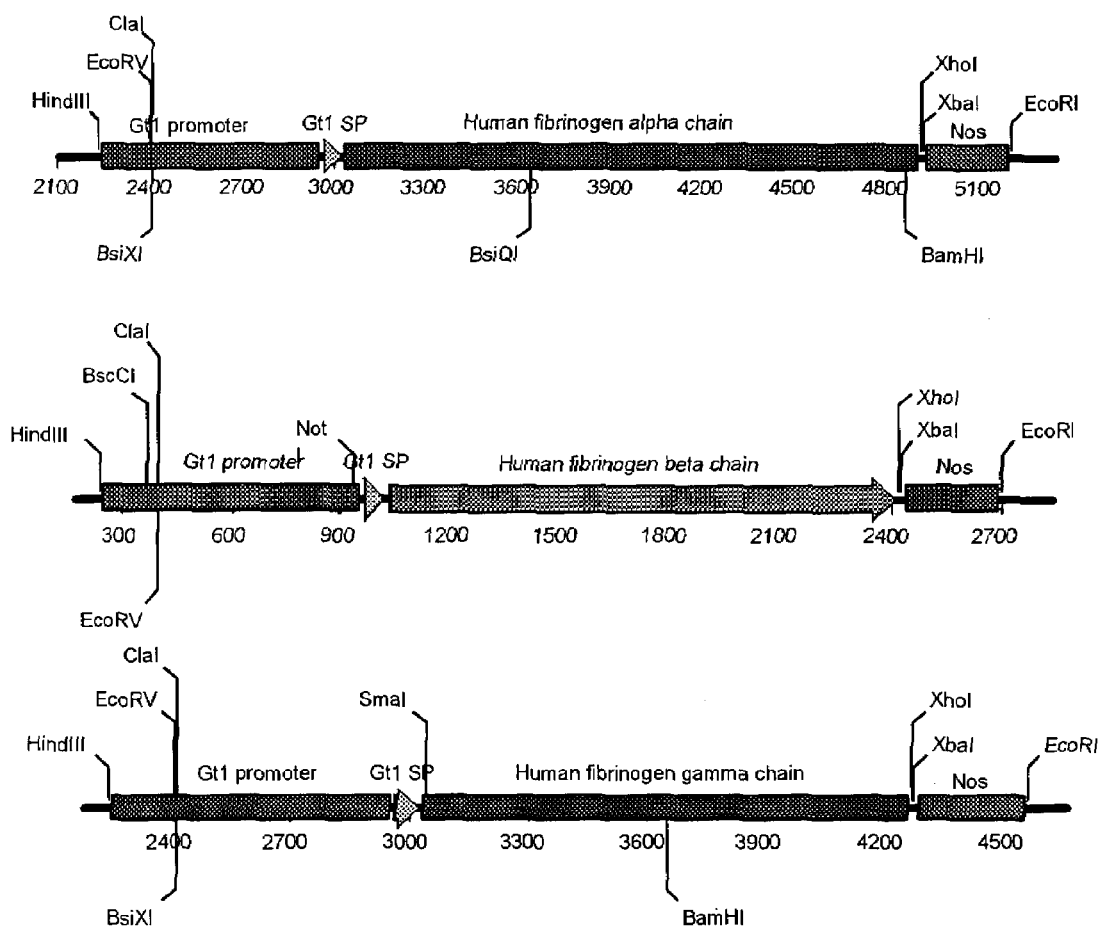

Figure 2. Western blot analysis of independent transgenic rice lines expressing individual subunits of human fibrinogen.
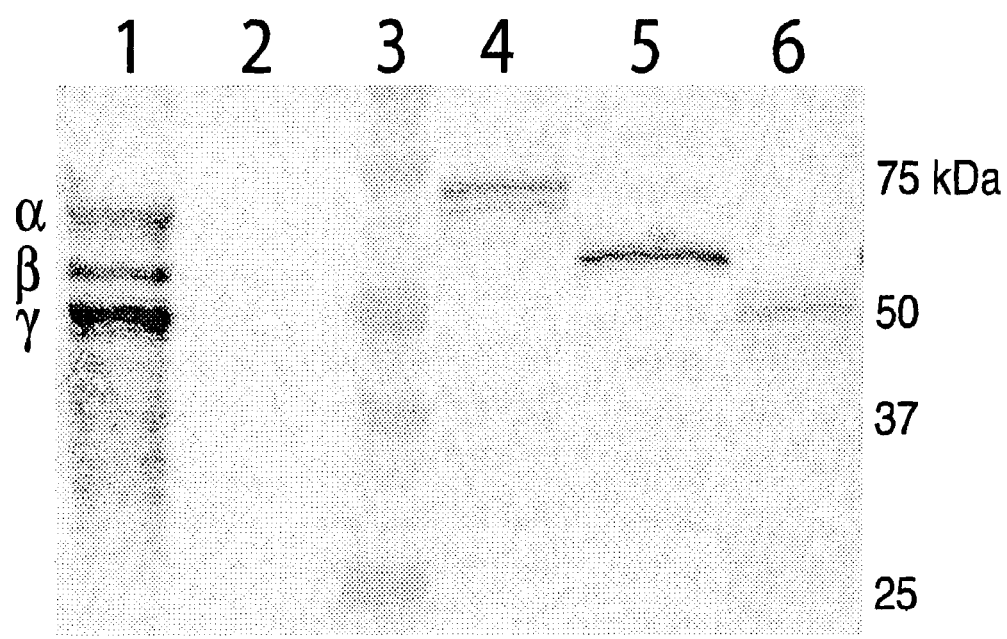

Figure 3. Expression of the fibrinogen polypeptide subunits α,β and γ simultaneously in transgenic rice seeds extracted under non-denaturing and denaturing conditions.
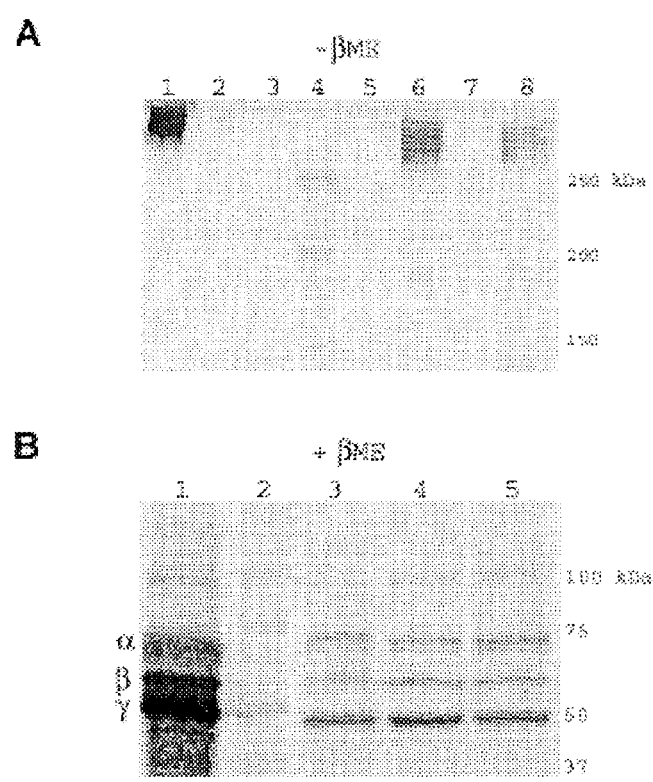

Figure 4. Construct showing the chimeric gene for the expression of alpha-1-antitrypsin in transgenic monocot seeds.

Figure 5. Coomassie-stained gel of total soluble proteins obtained from transgenic rice (var. Kitaake) seed extracts.
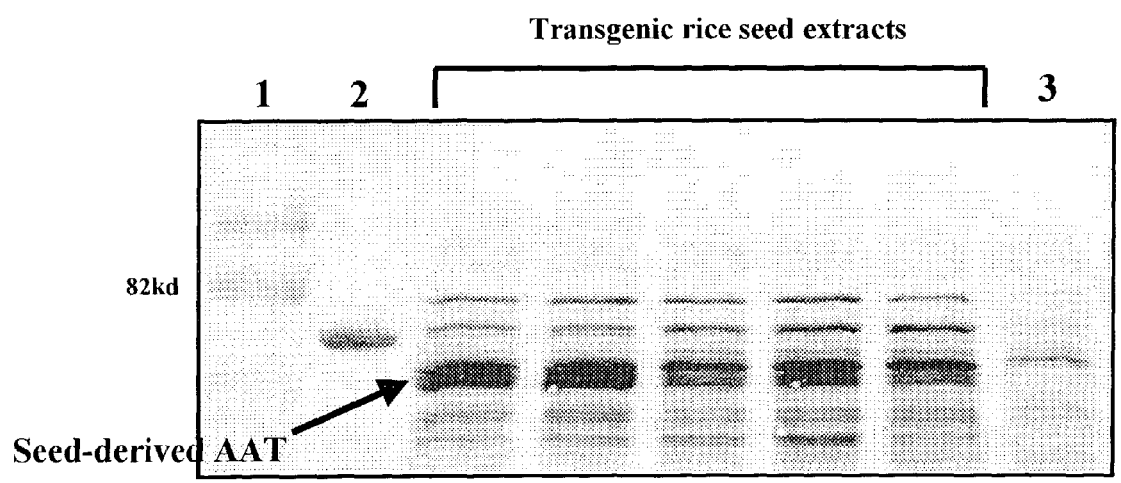

Figure 6. Western blot analysis of recombinant human AAT expressed in transgenic rice grains.
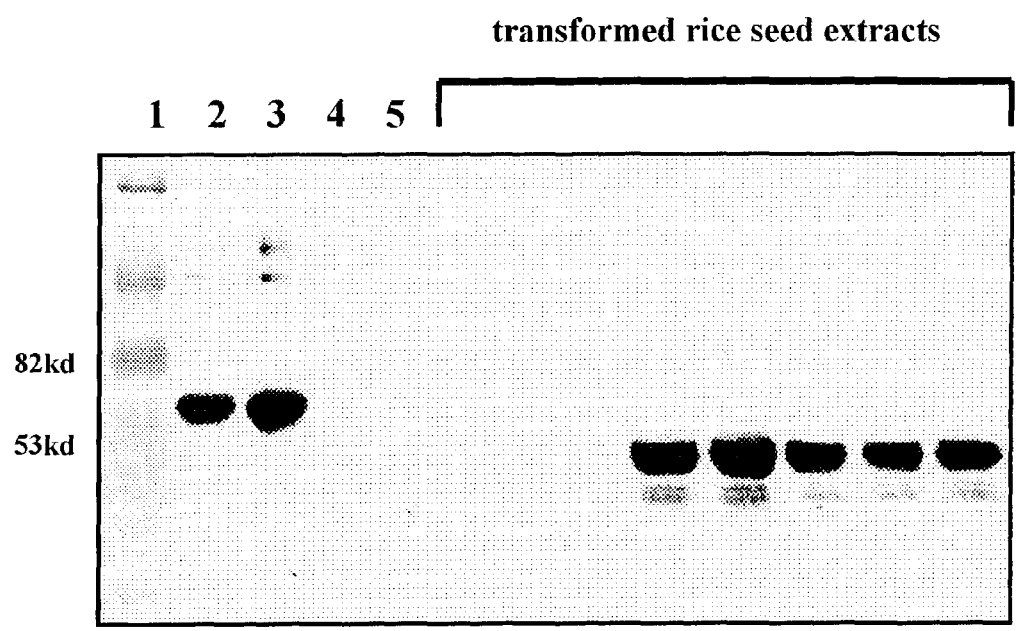

Figure 7. Activity of recombinant AAT against purified porcine elastase (PPE) as determined by Coomassie staining and Western blot analysis.
Panel A
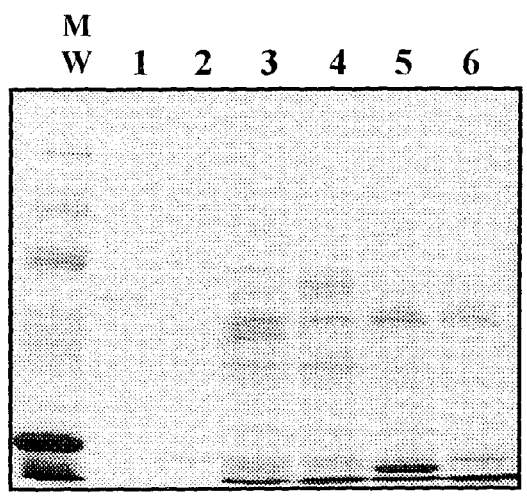
Panel B
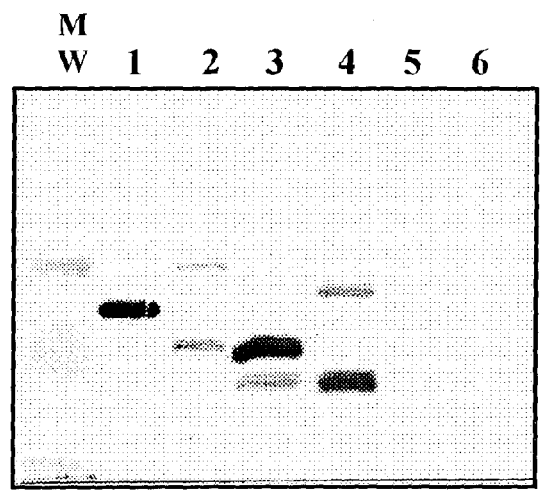

Figure 8. Purification of active AAT from inactive AAT via octyl-sepharose column chromotography.
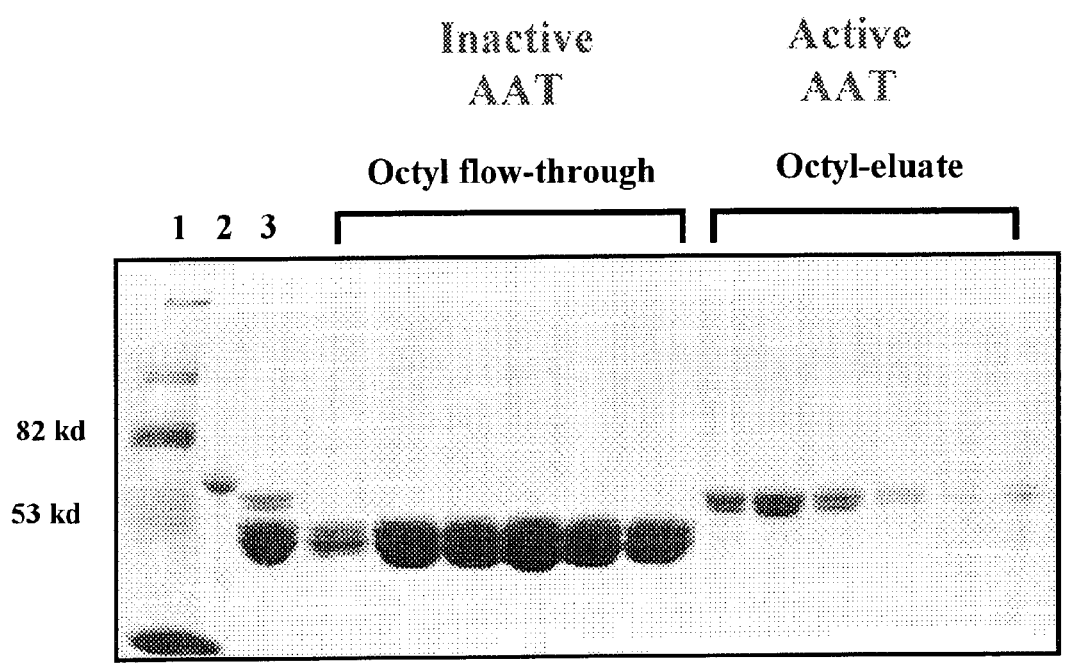

Figure 9. Initial biochemical characterization of AAT purified from rice seed extracts.
Panel A. Kinetics of elastase inhibition by AAT
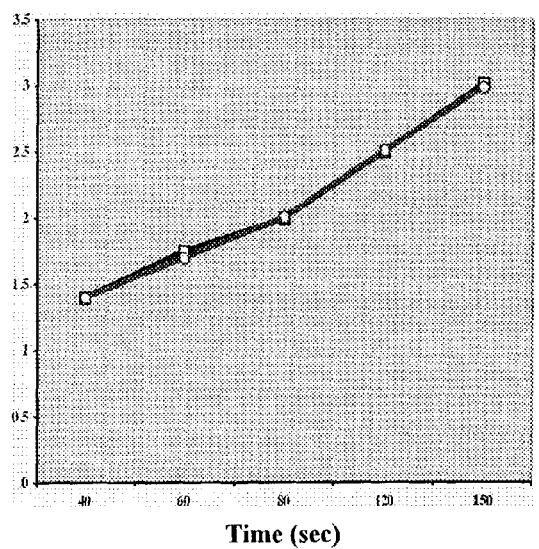
Time (sec)
Panel B. AAT Thermostability
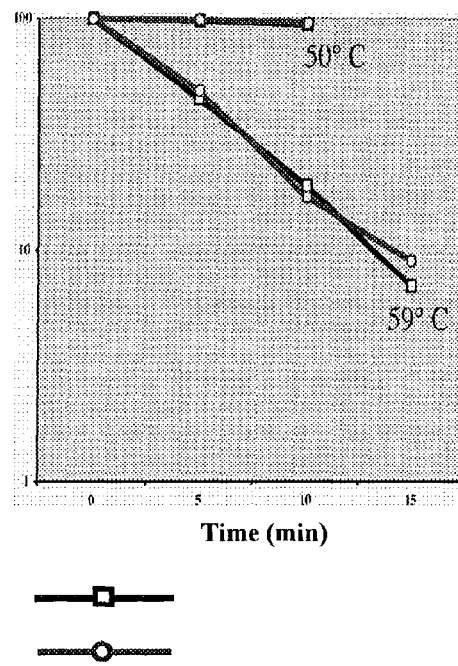
Time (min)
Native human AAT
Rice recombinant AAT

Fig 10. Construct map for the expression of human serum albumen in transgenic rice utilizing the Ramy 1A promoter.
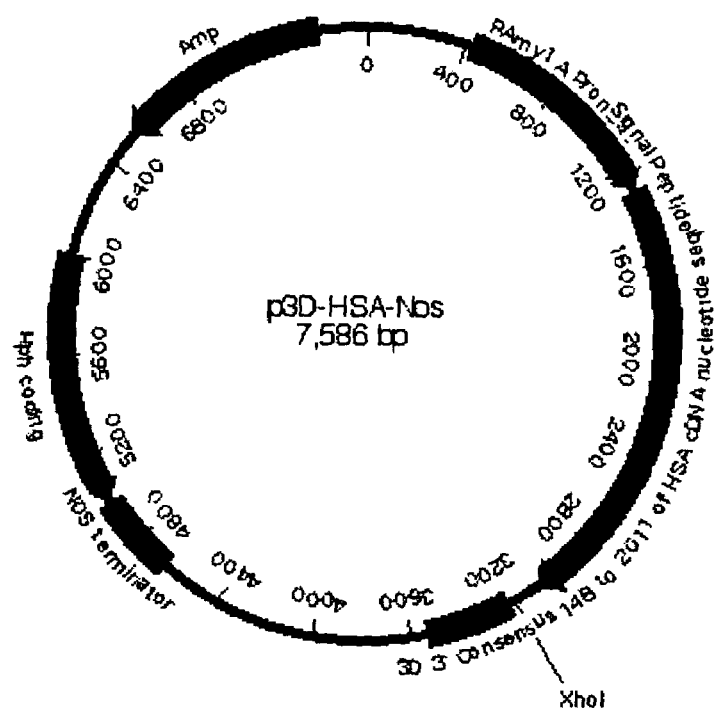

Figure 11. Western blot describing the expression of human serum albumen produced in transgenic rice seeds. Pooled seed from transgenic rice line 3-11-2 were imbibed in water for 24 hours, then 2μM gibberelic acid (GA) added.
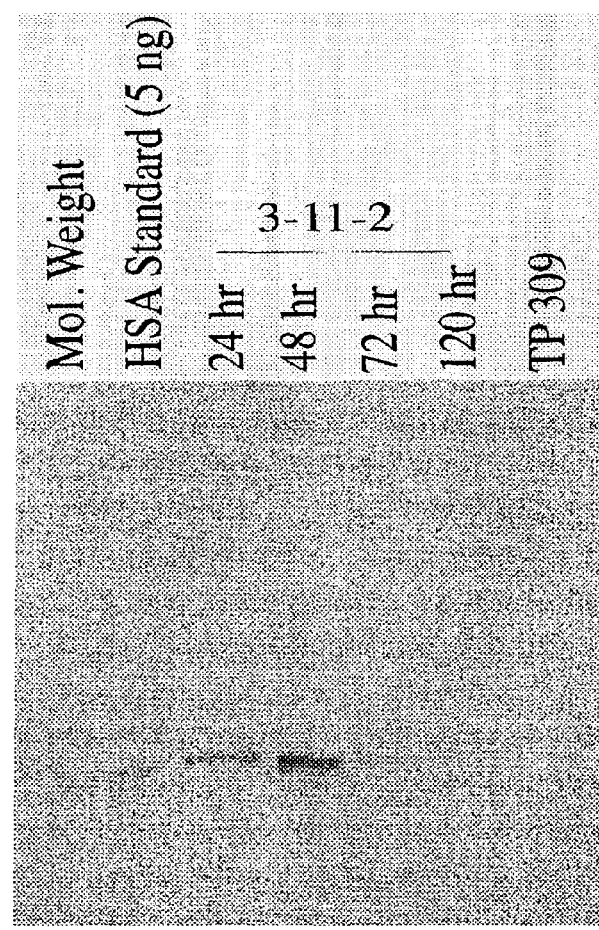

EXPRESSION OF HUMAN SERUM ALBUMIN (HSA) IN MONOCOT SEEDS

This application is a continuation-in-part of U.S. patent application Ser. No. 10/077,381, filed Feb. 14, 2002 now U.S. Pat. No. 6,991,824, which claims priority benefit to U.S. provisional application Ser. No. 60/269,199, filed Feb. 14, 2001, application Ser. No. 10/077,381 being a continuation-in-part of U.S. patent application Ser. No. 09/847,232, filed May 2, 2001 now abandoned, which claims priority benefit to U.S. provisional application Ser. No. 60/266,929, filed Feb. 6, 2001, and U.S. provisional application Ser. No. 60/201,182, filed May 2, 2000. All priority applications are incorporated herein by reference in their entirety.

FIELD OF THE INVENTION

The present invention relates to human blood proteins produced in the seeds of monocot plants for use in making human and animal topical compositions and human therapeutic compositions.

BACKGROUND OF THE INVENTION

Many human blood proteins are in short or limited supply due to the larger quantities required of the protein for positive therapeutic effect or possibly also due to the larger demand of these proteins by the world population of patients having the particular condition. It is also advantageous to produce blood proteins, normally extracted from blood products, from an alternative source such as crop plants. Production of blood proteins from plants mitigates contamination of the blood protein fraction with human viruses and other disease causative agents found in human or animal blood product fractions.

Blood proteins such as hemoglobin, alpha-1-antitrypsin ("AAT"), fibrinogen, human serum albumin, thrombin, antithrombin III, antibodies, blood coagulation factors (e.g. Factors V-XIII), and others are known to have therapeutic potential for a number of human conditions.

Hemoglobin is the major blood component molecule transporting oxygen to cells. Mammmalian hemoglobins are tetrameric proteins made up of two $\alpha$-like polypeptide subunits and two non-$\alpha$ (usually $\beta$, $\gamma$, or $\delta$) subunits. These subunits differ in primary amino acid sequence, but have similar secondary and tertiary structures. Each globin subunit has associated with it, by noncovalent interaction, a $Fe^{2+}$-porphyrin complex known as a heme group, to which oxygen binds. The predominant hemoglobin in adult erythrocytes is $\alpha 2\beta 2$, known as hemoglobin $A_1$ (HbA). Each hemoglobin tetramer has a molecular weight of 64 kD and each $\alpha$-like and $\beta$-like chain has a molecular weight of approximately 15.7 kD (141 amino acids) and 16.5 kD (146 amino acids) respectively.

AAT belongs to the class of serpin inhibitors and is one of the major protease inhibitors in human plasma. AAT is a single 394 amino acid polypeptide having an approximate molecular mass of 52 kD, and contains about 15% carbohydrate in the native human form of the molecule. Concentrations of AAT in human plasma range from 1000-3000 mg/L and in human milk range from 100 to 400 mg/L. Its primary physiological role is the inhibition neutrophil elastase, with an insufficiency leading to the development of pulmonary emphysema. Excess production of elastase activity leads to emphysema, hepatitis and a variety of skin disorders. While the binding affinity of AAT is highest for human neutrophil elastase, it also has affinity for pancreatic proteases such as chymotrypsin and trypsin. The current primary source for the treatment of AAT deficiency is isolating AAT from human blood plasma.

Fibrinogen is involved in the blood coagulation cascade and is converted to fibrin by its interaction with the natural clotting agent thrombin. Fibrin is the major component of blood clotting. Mature human fibrinogen consists of two pairs of three independent polypeptide chains ($\alpha$, $\beta$ and $\gamma$) that are linked together by 29 intra- and intermolecular disulfide bonds forming a native protein of 340 kD and is present in human plasma at an approximate concentration of 2500 mg/L. Three-dimentional structural analysis of independent fibrinogen domains has provided detailed structural features giving important clues to human fibrinogen's multifunctional role. The fibrinogen polypeptides are approximately 72 kD ($\alpha$), 52 kD ($\beta$) and 48 kD ($\gamma$) respectively with the $\beta$ polypeptide chain determining native molecule assembly. The structure of fibrinogen features a number of structural and functional domains containing multiple binding sites that facilitate interactions with itself, other proteins, certain cell types and allow fibrinogen to participate in a number of important physiological processes including blood coagulation, inflammation, angiogenesis, wound closure, artheriogenesis and tumorigenesis. Fibrin formation from a clotting standpoint is mediated by the interaction of native fibrinogen with its natural clotting agents Factor XIII and thrombin in the presence of blood soluble calcium.

Albumin is a transport protein molecule that carries out many functions in mammalian serum biology, notably that of a carrier of hormones and other soluble ligands from site to site, and other activities that contribute largely to general mammalian biochemistry. Human serum albumin ("HSA") is also the major protein component of blood being actively present at serum concentrations of approximately 30,000-50,000 mg/L. HSA is a single polypeptide chain of 66.5 kD that is initially synthesized as a prepro-albumin molecule in the liver and released from the endoplasmic reticulum after N-terminal and C-terminal Golgi processing. The resultant mature protein is 585 amino acids in length. It has been shown that the natural preprosequnce of HSA can function in correct protein targeting/processing across a plant plasma membrane in transgenic tobacco leaves (Sijmons et al, 1990).

Prothrombin, a plasma glycoprotein, is the zymogen of the serine protease thrombin that catalyzes the conversion of fibrinogen to fibrin as well as several other reactions that may be important for blood coagulation. Prothrombin is a single polypeptide chain approximately 72,000 molecular weight in size. The complete human thrombin cDNA consists of 622 amino acid residues and includes a leader sequence of 36 amino acid residues. Active thrombin has an apparent molecular weight of 36,000 and is made up of two disulfide-linked polypeptide chains resulting from prothrombin cleavage. The proteolytic events leading to in vitro activation and conversion of human prothrombin to active thrombin have been extremely well characterized.

Antithrombin III is a single chain glycoprotein with a molecular weight of 58 kD. It is a member of the serpin (serine protease inhibitor) super family and is considered to be the most important inhibitor in the coagulation cascade. Antithrombin III inhibits a wide spectrum of serine proteases including thrombin, factors IXa, Xa and XIa, kallikrein, plasmin, urokinase, C1-esterase, and trypsin. Antithrombin III activity is markedly potentiated by heparin; potentiation of its activity is the principle mechanism by which both heparin and low-molecular-weight heparin produce anticoagulation.

Factors V-XIII are proteins (mostly proteases in their active states) that are involved in the intrinsic pathway of the classical casade mechanism for blood coagulation. The majority of these molecules exist as precursors that are processed in an ordered sequence of transformations from inactive to catalytically active forms. Factor V is proaccelerin (the accelerator globulin) while Factor VI is the activated form of Factor V. Factor VII is proconvertin, the plasma thromboplastin component, while Factors VIII (antihemophilic factor) and IX (Christmas antihemophilic factor) are both associated with the hemophilia disease state. Factors X (Stuart-Power factor), XI (plasma thromboplastin anticedent) and XII (Hageman factor) are all involved with the maturation/stabilization of thrombin. Factor XIII (fibrin stabilizing factor) is a plasma transglutaminase directly acting on fibrin during the clotting process. All these Factors are present at relatively low in serum plasma (0.001 to 50 mg/L). Other protein factors also involved in the blood coagulation cascade include Fletcher Factor (prekallikrein), Fitzgerald factor (kininogen) and von Willebrand Factor.

Immunoglobulins (antibodies) present in humans act to confer resistance to a variety of pathogens to which a patient may have been exposed. Immunoglobulin molecules account for 15-20% of the mass in human serum and consist predominantly of IgG, IgM and IgA-type antibodies involved in fighting various infections that invade the blood system and potentially the rest of the body. IgG type antibodies are the most prevelant and exist at a serum concentration of between 6-18 g/L. The blood system also serves as a carrier directing these molecules to specific areas of the body to combat resulting infections and potential oncogenic targets. Mature antibodies consist of two polypeptides (light and heavy chains) that must be expressed in eqimolar amounts and come together to form functional entities. The light chain (~25 kD) is a protein of ~210-240 amino acids in length while the heavy chain (~50 kD) is a protein of ~450-460 amino acids in length. Both light and heavy chains carry signal peptides for processing and secretion into the blood stream. Expression of monoclonal antibodies in plants is of particular interest, because it requires the expression of two genes, synthesis of two proteins and coerrect assembly of the tetrameric protein to result in a functional antibody.

Initial studies of antibodies in plants focused on the IgG antibodiy class (Hiatt et al, 1989; Hiatt and Ma, 1992); but later studies explored the in planta expression of complex antibody molecules such as secretory IgA antibodies (4 genes) and more complex antibody forms (Ma et al, 1995; Vine et al, 2001).

U.S. Pat. Nos. 6,417,429, 5,959,177, 5,639,947 and 5,202,422, all related patents, disclose the production of antibody molecules in transgenic tobacco plant leaves.

U.S. Pat. No. 6,303,341 discloses the production of immunoglobulins containing protection proteins in tobacco plant leaves, stems, flowers and roots.

Published U.S. Patent Application U.S. 2002/0,174,453 discloses the production of antibodies in the plastids of tobacco plants.

Published U.S. Patent Application U.S. 2002/0,046,418 discloses a controlled environment agriculture bioreactor for the commercial production of heterologous proteins in transgenic plants. The specification discloses that production of mammalian blood proteins can be achieved. Example 7 discloses the production of human blood factors in the leaves of potato, tobacco and alfalfa plants.

U.S. Pat. No. 6,344,600 discloses the production of hemoglobin and myoglobin in tobacco plant leaves. Example X discloses the extraction and partial purification of recombinant hemoglobin from tobacco seeds. The expression was obtained by transformation of the coexpression plasmid pBIOC59, which was constructed to allow targeting in the chloroplasts, and contained for this purpose the transit peptide of the precursor of the small subunit of ribulose 1,5-diphosphate carboxylase of *Pisum sativum* L. Expression in seeds was reported to be at a maximum level of 0.05% recombinant hemoglobin relative to the total soluble proteins extracted.

Example XI of the '600 patent discloses the construction of plasmids containing one of the α or β chains of hemoglobin allowing constitutive expression or expression in the albumin in maize seeds. According to this disclosure, the constitutive or albumin-specific expression of the hemoglobin chains required the following regulatory sequences: one of three promoters allowing a constitutive expression ((i) the rice actin promoter followed by the rice actin intron, contained in the plasmid pAct1-F4; (ii) the 35S double constitutive promoter of cauliflower mosaic virus; or (iii) the promoter of the maize γ-zein gene contained in the plasmid pγ63) and one of two terminators ((i) the 35S polyA terminator; or (ii) the NOS polyA terminator). No experiment or data is provided regarding transformation or expression of these plasmids in maize or maize seeds.

U.S. Pat. No. 5,767,363 discloses the use of a seed-specific promoter derived from ACP of *Brassica napus*, to affect and vary the expression of seed oils in rape and tobacco plants. The specification generically discloses that the seed-specific promoter can be used for the expression of pharmaceutical proteins, such as blood factors or human serum albumin, however no experimental data whatsoever is presented in this regard.

Daniell et al. (2001) is a review article discussing recent developments in the field of medical molecular farming, including the production of antibodies and proteins in plants.

None of these patents or publications discloses the production of human blood proteins in monocot seeds in high yield. It is desirable to provide for the production of human blood proteins in high yield free from contaminating source agents in order to provide the patient population with sufficient supply of these proteins for use in treating humans with conditions treatable by administration of a particular blood protein.

SUMMARY OF THE INVENTION

In one aspect, the invention includes a method of producing a recombinant human blood protein in monocot plant seeds, comprising the steps of:

(a) transforming a monocot plant cell with a chimeric gene comprising (i) a promoter from the gene of a maturation-specific monocot plant storage protein, (ii) a first DNA sequence, operably linked to said promoter, encoding a monocot plant seed-specific signal sequence capable of targeting a polypeptide linked thereto to a monocot plant seed endosperm cell, and (iii) a second DNA sequence, linked in translation frame with the first DNA sequence, encoding a human blood protein, wherein the first DNA sequence and the second DNA sequence together encode a fusion protein comprising an N-terminal signal sequence and the human blood protein;

(b) growing a monocot plant from the transformed monocot plant cell for a time sufficient to produce seeds containing the human blood protein; and (c) harvesting the seeds from the plant, wherein the human blood protein constitutes at least 3.0% of the total soluble protein in the harvested seeds.

The invention also includes a purified human blood protein obtained by the method. Preferably, the human blood protein comprises one or more plant glycosyl groups.

The invention also provides a monocot plant seed product, preferably selected from whole seed, flour, extract and malt, prepared from the harvested seeds obtained by the method of the invention. Preferably, the human blood protein constitutes at least 3.0% of the total soluble protein in the seed product.

The invention further provides a composition comprising a purified human blood protein, preferably comprising at least one plant glycosyl group, and at least one pharmaceutically acceptable excipient or nutrient, wherein the human blood protein is produced in a monocot plant containing a nucleic acid sequence encoding the human blood protein and is purified from seed harvested from the monocot plant. The nutrient is from a source other than the monocot plant. The formulation can be used for parenteral, enteric, inhalation, intranasal or topical delivery.

These and other objects and features of the invention will become more fully apparent when the following detailed description of the invention is read in conjunction with the accompanying drawings and claims.

BRIEF DESCRIPTION OF THE FIGURES

FIG. 1 shows plasmids with constructs containing three codon-optimized genes encoding the fibrinogen polypeptides α (pAPI 398), β (pAPI 417) and γ (pAPI 327) (SEQ ID NO: 1-3), each under the control of the rice glutelin promoter Gt1. These plasmids, including a plasmid (not shown) containing the hygromycin selectable marker, were bombarded into embryogenic rice callus to create transgenic rice plants expressing these three genes in mature rice seeds.

FIG. 2 shows a Western blot analysis of transgenic rice lines expressing individual subunits of human fibrinogen. Lane 1, positive control, purified native human fibrinogen (obtained from the Red Cross) showing all three polypeptide chains; Lane 2, extract from Tapei 309, a non transgenic rice variety; Lane 3, molecular weight standard; Lane 4, rice seed extract expressing fibrinogen α chain; Lane 5, rice seed extract expressing fibrinogen β chain; Lane 6, rice seed extract expressing fibrinogen γ chain. Total protein extract of rice seeds was performed in 2% SDS, 1M urea, 1% βMe and PBS pH 7.4. Fibrinogen polypeptides were detected using antibody recognizing all three chains or individual chains only.

FIG. 3 shows the simultaneous expression of the three fibrinogen polypeptide chains (α, β and γ) in transgenic rice seeds and analyzed via Western blot analysis. Fibrinogen polypeptides and protein aggregates were detected using antibody recognizing all three chains. FIG. 3A indicates total protein extracted from rice seeds under non-denaturing conditions (350 mM NaCl, PBS pH 7.4, 0.01% Tween-20/ Triton X-100/CHAPS) and run on a non-denaturing 10% acrylamide gel. Lane 1, 1 µg purified human fibrinogen; Lanes 2 & 3, extracts from Tapei 309, a non-transgenic rice variety; Lane 4, molecular weight markers; Lanes 5 & 7, extracts from two transgenic rice lines where 1.0% βMe was included in the extraction buffer; lanes 6 & 8, extracts from two transgenic rice lines without βMe in the extraction buffer. Lanes 6 & 8 show large protein aggregates that were extracted under non-denaturing conditions from the transgenic lines that run at the approximate position of complexed native human fibrinogen. FIG. 3B indicates total protein extracted from rice seeds in 2% SDS, 1M urea, 1% βMe and PBS pH 7.4, and run on SDS-PAGE. Lane 1, positive control, native human fibrinogen (obtained from the Red Cross) showing all three polypeptide chains; Lane 2, molecular weight standards; Lanes 3-5, three independent transgenic rice lines expressing all three fibrinigen polypeptides.

FIG. 4 shows the plasmid pAPI 250 expressing the codon-optimized gene for alpha-1-antitrypsin (AAT) (SEQ ID NO: 5) under the control of the rice glutelin promoter Gt1. This plasmid, along with a plasmid (not shown) containing the hygromycin selectable marker gene, was bombarded into embryogenic rice callus to create transgenic rice plants expressing AAT in mature rice seeds.

FIG. 5 shows Coomassie brilliant blue staining of aqueous phase extraction of transgenic rice grains expressing human recombinant AAT. Both untransformed (rice var. Kitaake) and transgenic rice seeds (~10 pooled R1 seed from five individual transgenic plants) were ground with PBS pH 7.4 buffer. The resulting extract was spun at 14,000 rpm at 4° C. for 10 min. Supernatant was collected and ~20 µg of this soluble protein extract was resuspended in sample loading buffer, and loaded onto a precast SDS-PAGE gel. Lane 1, molecular weight protein markers; Lane 2, purified non-recombinant human AAT; Lane 3, extract from control non-transformed Kitaake variety. Between lanes 2 and 3, the results from the extracts of the five individual transgenic plants are shown.

FIG. 6 shows Western blot analysis of recombinant human AAT expressed in transgenic rice grains. The R1 pooled seed soluble protein extracts (~10 µg total protein) from seven independent transgenic rice transformants were prepared as described in FIG. 5 above, separated by SDS-PAGE gel and then blotted onto a nitrocellulose filter. The identification of AAT expressed in rice seeds was carried out by Western analysis using anti-AAT antibody. Lane 1, molecular weight protein markers; Lanes 2 & 3, 1 µg and 2 µg, respectively, of purified non-recombinant human AAT; Lanes 4 & 5, control, non-transgenic rice extract (var. Kitaake). The final seven lanes show the results from the extracts of the seven individual transgenic plants. Extracts from two of the seven transgenic lines did not express AAT. The shift in gel mobility between the non-recombinant human and recombinant rice-expressed forms is due to the type and glycosylation differences in the human and recombinant rice-expressed proteins.

FIG. 7 shows activity of purified recombinant AAT (rAAT) obtained from rice extracts against purified porcine pancreatic elastase (PPE) as determined by Coomassie staining and Western blot analysis. The activity of rAAT is demonstrated by a band shift assay involving the AAT protease substrate, elastase. AAT samples from human and rice ectracts were incubated with equal number of moles of PPE at 37° C. for 15 min. Negative control for band shift assay was prepared with the AAT samples incubated with equal volume of PPE added. Lane MW refers to molecular weight markers. FIG. 7A: Lane 1, purified non-recombinant AAT from human plasma; Lane 2, purified AAT from human plasma+PPE; Lane 3, soluble protein extract containing AAT from transgenic rice seed; Lane 4, protein extract containing AAT from transgenic rice seed+PPE; Lane 5, non-transformed rice seed extract; Lane 6, non-transformed rice seed extract+PPE. FIG. 7B shows a shifted band in Lanes 1, 2 and 3. The shifted band, a complex between PPE and an AAT fragment is confirmed to contain AAT by Western blot analysis. The lanes in FIG. 7B are analogous to those in FIG. 7A.

FIG. 8 depicts AAT derived from rice cell extracts purified initially through Con-A and DEAE Sepharose respectively, then loaded onto an octyl Sepharose column. Octyl Sepharose is the final purification step and separates active AAT from an inactivated form of the protein. Lane 1, molecular weight markers; Lane 2, 2 µg purified non-recombinant human AAT as a standard; Lane 3, pooled eluate from the DEAE Sepharose column. The remaining columns show the flow-through and the eluate from the octyl Sepharose column. Approximately 50 µL from each column fraction was loaded onto an SDS-PAGE gel and the proteins visualized by Coomassie staining. Octyl Sepharose flow-through shows the inactive AAT protein while the eluate resolves active AAT.

FIG. 9A depicts an AAT association rate constant for activity of purified recombinant AAT against PPE determined (as described by the procedure in FIG. 7) using non-recombinant human AAT as a control. Data were generated by Coomassie protein staining and Western blot analysis, as described in FIG. 7. FIG. 9B depicts the thermostability of plant-derived recombinant AAT versus native human AAT determend by the PPE inhibition assay.

FIG. 10 shows the plasmid pAPI 9 for expression of codon-optimized human serum albumin (HSA) (SEQ ID NO: 4) under the control of the rice Amy1A promoter/signal peptide. This plasmid is useful for the expression of HSA in germinated rice seeds.

FIG. 11 shows the expression of HSA in transgenic rice seeds. Pooled seed from transgenic rice line 3-11-2 were imbibed in water for 24 hours, then 2 µM gibberelic acid (GA) was added. Seed samples were extracted at 24, 48, 72, and 120 hours post GA addition and soluble proteins were extracted and prepared for Western analysis. 15 µg of soluble protein were loaded onto each lane along with protein isolated from the non-transfromed negative control line TP309. The blot was probed with monoclonal antibody prepared against HSA.

DETAILED DESCRIPTION OF THE INVENTION

Unless otherwise indicated, all terms used herein have the meanings given below or are generally consistent with same meaning that the terms have to those skilled in the art of the present invention. Practitioners are particularly directed to Sambrook et al. (1989) Molecular Cloning: A Laboratory Manual (Second Edition), Cold Spring Harbor Press, Plainview, N.Y., Ausubel F M et al. (1993) Current Protocols in Molecular Biology, John Wiley & Sons, New York, N.Y., and Gelvin and Schilperoot, eds. (1997) Plant Molecular Biology Manual, Kluwer Academic Publishers, The Netherlands for definitions and terms of the art.

The polynucleotides of the invention may be in the form of RNA or in the form of DNA, and include messenger RNA, synthetic RNA and DNA, cDNA, and genomic DNA. The DNA may be double-stranded or single-stranded, and if single-stranded may be the coding strand or the non-coding (anti-sense, complementary) strand.

The term "stably transformed" with reference to a plant cell means the plant cell has a non-native (heterologous) nucleic acid sequence integrated into its genome which is maintained through two or more generations.

By "host cell" is meant a cell containing a vector and supporting the replication and/or transcription and/or expression of the heterologous nucleic acid sequence. Preferably, according to the invention, the host cell is a monocot plant cell. Other host cells may be used as secondary hosts, including bacterial, yeast, insect, amphibian or mammalian cells, to move DNA to a desired plant host cell.

A "plant cell" refers to any cell derived from a plant, including undifferentiated tissue (e.g., callus) as well as plant seeds, pollen, propagules, embryos, suspension cultures, meristematic regions, leaves, roots, shoots, gametophytes, sporophytes and microspores.

The term "mature plant" refers to a fully differentiated plant.

The term "seed product" includes, but is not limited to, seed fractions such as de-hulled whole seed, flour (seed that has been de-hulled by milling and ground into a powder) a seed extract, preferably a protein extract (where the protein fraction of the flour has been separated from the carbohydrate fraction), malt (including malt extract or malt syrup) and/or a purified protein fraction derived from the transgenic grain.

The term "biological activity" refers to any biological activity typically attributed to that protein by those of skill in the art.

The term "blood protein" refers to one or more proteins, or biologically active fragments thereof, found in normal human blood, including, without limitation, hemoglobin, alpha-1-antitrypsin, fibrinogen, human serum albumin, prothrombin/thrombin, antithrombin III, antibodies, blood coagulation factors (Factor V, Factor VI, Factor VII, Factor VIII, Factor IX, Factor X, Factor XI, Factor XII, Factor XIII, Fletcher Factor, Fitzgerald Factor and von Willebrand Factor), and biologically active fragments thereof.

The term "non-nutritional" refers to a pharmaceutically acceptable excipient which does not as its primary effect provide nutrition to the recipient. Preferably, it may provide one of the following services to an enterically delivered formulation, including acting as a carrier for a therapeutic protein, protecting the protein from acids in the digestive tract, providing a time-release of the active ingredients being delivered, or otherwise providing a useful quality to the formulation in order to administer to the patient the blood proteins.

"Monocot seed components" refers to carbohydrate, protein, and lipid components extractable from monocot seeds, typically mature monocot seeds.

"Seed maturation" refers to the period starting with fertilization in which metabolizable reserves, e.g., sugars, oligosaccharides, starch, phenolics, amino acids, and proteins, are deposited, with and without vacuole targeting, to various tissues in the seed (grain), e.g., endosperm, testa, aleurone layer, and scutellar epithelium, leading to grain enlargement, grain filling, and ending with grain desiccation.

"Maturation-specific protein promoter" refers to a promoter exhibiting substantially upregulated activity (greater than 25%) during seed maturation.

"Heterologous DNA" refers to DNA which has been introduced into plant cells from another source, or which is from a plant source, including the same plant source, but which is under the control of a promoter that does not normally regulate expression of the heterologous DNA.

"Heterologous protein" is a protein encoded by a heterologous DNA.

A "signal sequence" is an N- or C-terminal polypeptide sequence which is effective to localize the peptide or protein to which it is attached to a selected intracellular or extracellular region. Preferably, according to the invention, the signal sequence targets the attached peptide or protein to a location such as an endosperm cell, more preferably an endosperm-cell organelle, such as an intracellular vacuole or other protein storage body, chloroplast, mitochondria, or endoplasmic reticulum, or extracellular space, following secretion from the host cell.

Expression vectors for use in the present invention are chimeric nucleic acid constructs (or expression vectors or cassettes), designed for operation in plants, with associated upstream and downstream sequences.

In general, expression vectors for Use in practicing the invention include the following operably linked components that constitute a chimeric gene: a promoter from the gene of a maturation-specific monocot plant storage protein, a first DNA sequence, operably linked to the promoter, encoding a monocot plant seed-specific signal sequence (such as an N-terminal leader sequence or a C-terminal trailer sequence) capable of targeting a polypeptide linked thereto to an endosperm cell, preferably an endosperm-cell organelle, such as a protein storage body, and a second DNA sequence, linked in translation frame with the first DNA sequence, encoding a human blood protein. The signal sequence is preferably cleaved from the human blood protein in the plant cell.

The chimeric gene, in turn, is typically placed in a suitable plant-transformation vector having (i) companion sequences upstream and/or downstream of the chimeric gene which are of plasmid or viral origin and provide necessary characteristics to the vector to permit the vector to move DNA from bacteria to the desired plant host; (ii) a selectable marker sequence; and (iii) a transcriptional termination region generally at the opposite end of the vector from the transcription initiation regulatory region.

Numerous types of appropriate expression vectors, and suitable regulatory sequences are known in the art for a variety of plant host cells. The promoter region is chosen to be regulated in a manner allowing for induction under seed-maturation conditions. In one aspect of this embodiment of the invention, the expression construct includes a promoter which exhibits specifically upregulated activity during seed maturation. Promoters for use in the invention are typically derived from cereals such as rice, barley, wheat, oat, rye, corn, millet, triticale or sorghum. Examples of such promoters include the maturation-specific promoter region associated with one of the following maturation-specific monocot plant storage proteins: rice glutelins, oryzins, and prolamines, barley hordeins, wheat gliadins and glutelins, maize zeins and glutelins, oat glutelins, and sorghum kafirins, millet pennisetins, and rye secalins. Exemplary regulatory regions from these genes are exemplified by SEQ ID NOS: 6-14. Other promoters suitable for expression in maturing seeds include the barley endosperm-specific B1-hordein promoter, GluB-2 promoter, Bx7 promoter, Gt3 promoter, GluB-1 promoter and Rp-6 promoter, particularly if these promoters are used in conjunction with transcription factors.

Of particular interest is the expression of the nucleic acid encoding a human blood protein from a promoter that is preferentially expressed in plant seed tissue. Examples of such promoter sequences include those sequences derived from sequences encoding plant storage protein genes or from genes involved in fatty acid biosynthesis in oilseeds. Exemplary preferred promoters include a glutelin (Gt1) promoter, as exemplified by SEQ ID NO: 6, which effects gene expression in the outer layer of the endosperm, and a globulin (Glb) promoter, as exemplified by SEQ ID NO: 7, which effects gene expression in the center of the endosperm. Promoter sequences for regulating transcription of gene coding sequences operably linked thereto include naturally-occurring promoters, or regions thereof capable of directing seed-specific transcription, and hybrid promoters, which combine elements of more than one promoter. Methods for construction such hybrid promoters are well known in the art.

In some cases, the promoter is native to the same plant species as the plant cells into which the chimeric nucleic acid construct is to be introduced. In other embodiments, the promoter is heterologous to the plant host cell.

Alternatively, a seed-specific promoter from one type of monocot may be used regulate transcription of a nucleic acid coding sequence from a different monocot or a non-cereal monocot.

In addition to encoding the protein of interest, the expression cassette or heterologous nucleic acid construct includes DNA encoding a signal peptide that allows processing and translocation of the protein, as appropriate. Exemplary signal sequences are those sequences associated with the monocot maturation-specific genes: glutelins, prolamines, hordeins, gliadins, glutenins, zeins, albumin, globulin, ADP glucose pyrophosphorylase, starch synthase, branching enzyme, Em, and lea. Exemplary sequences encoding a signal peptide for a protein storage body are identified herein as SEQ ID NOS: 15-21.

In one preferred embodiment, the method is directed toward the localization of proteins in an endosperm cell, preferably an endosperm-cell organelle, such as a protein storage body, mitochondrion, endoplasmic reticulum, vacuole, chloroplast or other plastidic compartment. For example, when proteins are targeted to plastids, such as chloroplasts, in order for expression to take place the construct also employs the use of sequences to direct the gene product to the plastid. Such sequences are referred to herein as chloroplast transit peptides (CTP) or plastid transit peptides (PTP). In this manner, when the gene of interest is not directly inserted into the plastid, the expression construct additionally contains a gene encoding a transit peptide to direct the gene of interest to the plastid. The chloroplast transit peptides may be derived from the gene of interest, or may be derived from a heterologous sequence having a CTP. Such transit peptides are known in the art. See, for example, (Smeekens et al., 1986; Wasmann et al., 1986; Von Heijne et al., 1991, U.S. Pat. Nos. 4,940,835 and 5,728,925; . Additional transit peptides for the translocation of the protein to the endoplasmic reticulum (ER) (Chrispeels, 1991; Vitale and Chrispeels, 1992), nuclear localization signals (Shieh et al., 1993; Varagona et al., 1992)or vacuole (Raikhel and Chrispeels 1992; Bednarek and Raikel, 1992; also see U.S. Pat. No. 5,360,726) may also find use in the constructs of the present invention.

Another exemplary class of signal sequences are sequences effective to promote secretion of heterologous protein from aleurone cells during seed germination, including the signal sequences associated with alpha-amylase, protease, carboxypeptidase, endoprotease, ribonuclease, DNase/RNase, (1-3)-beta-glucanase, (1-3)(1-4)-beta-glucanase, esterase, acid phosphatase, pentosamine, endoxylanase, β-xylopyranosidase, arabinofuranosidase, beta-glucosidase, (1-6)-beta-glucanase, perioxidase, and lysophospholipase.

Since many protein storage proteins are under the control of a maturation-specific promoter, and this promoter is operably linked to a signal sequence for targeting to a protein body, the promoter and signal sequence can be isolated from a single protein-storage gene, then operably linked to a blood protein in the chimeric gene construction. One preferred and exemplary promoter-signal sequence is from the rice Gt1 gene, having an exemplary sequence identified by SEQ ID NO: 6. Alternatively, the promoter and leader sequence may be derived from different genes. One preferred and exemplary promoter-signal sequence combination is the rice Glb promoter linked to the rice Gt1 leader sequence, as exemplified by SEQ ID NO: 7.

Preferably, expression vectors or heterologous nucleic acid constructs designed for operation in plants comprise companion sequences upstream and downstream to the expression cassette. The companion sequences are of plasmid or viral origin and provide necessary characteristics to the vector to permit the vector to move DNA from a secondary host to the plant host, such as, sequences containing an origin of replication and a selectable marker. Typical secondary hosts include bacteria and yeast.

In one embodiment, the secondary host is *E. coli*, the origin of replication is a ColE1-type, and the selectable marker is a gene encoding ampicillin resistance. Such sequences are well known in the art and are commercially available as well (e.g., Clontech, Palo Alto, Calif.; Stratagene, La Jolla, Calif.).

The transcription termination region may be taken from a gene where it is normally associated with the transcriptional initiation region or may be taken from a different gene. Exemplary transcriptional termination regions include the NOS terminator from *Agrobacterium* Ti plasmid and the rice α-amylase terminator.

Polyadenylation tails may also be added to the expression cassette to optimize high levels of transcription and proper transcription termination, respectively. Polyadenylation sequences include, but are not limited to, the *Agrobacterium* octopine synthetase signal, or the nopaline synthase of the same species.

Suitable selectable markers for selection in plant cells include, but are not limited to, antibiotic resistance genes, such as, kanamycin (nptil), G418, bleomycin, hygromycin, chloramphenicol, ampicillin, tetracycline, and the like. Additional selectable markers include a bar gene which codes for bialaphos resistance; a mutant EPSP synthase gene which encodes glyphosate resistance; a nitrilase gene which confers resistance to bromoxynil; a mutant acetolactate synthase gene (ALS) which confers imidazolinone or sulphonylurea resistance; and a methotrexate resistant DHFR gene.

The particular marker gene employed is one which allows for selection of transformed cells as compared to cells lacking the DNA which has been introduced. Preferably, the selectable marker gene is one which facilitates selection at the tissue culture stage, e.g., a kanamyacin, hygromycin or ampicillin resistance gene.

The vectors of the present invention may also be modified to include intermediate plant transformation plasmids that contain a region of homology to an *Agrobacterium tumefaciens* vector, a T-DNA border region from *Agrobacterium tumefaciens*, and chimeric genes or expression cassettes (described above). Further, the vectors of the invention may comprise a disarmed plant tumor inducing plasmid of *Agrobacterium tumefaciens*.

In general, a selected nucleic acid sequence is inserted into an appropriate restriction endonuclease site or sites in the vector. Standard methods for cutting, ligating and transformation into a secondary host cell, known to those of skill in the art, are used in constructing vectors for use in the present invention. (See generally, Maniatis et al., Ausubel et al., and Gelvin et al., supra.)

Plant cells or tissues are transformed with expression constructs (heterologous nucleic acid constructs, e.g., plasmid DNA into which the gene of interest has been inserted) using a variety of standard techniques. Effective introduction of vectors in order to facilitate enhanced plant gene expression is an important aspect of the invention. It is preferred that the vector sequences be stably transformed, preferably integrated into the host genome.

The method used for transformation of host plant cells is not critical to the present invention. The skilled artisan will recognize that a wide variety of transformation techniques exist in the art, and new techniques are continually becoming available. Any technique that is suitable for the target host plant may be employed within the scope of the present invention. For example, the constructs can be introduced in a variety of forms including, but not limited to, as a strand of DNA, in a plasmid, or in an artificial chromosome. The introduction of the constructs into the target plant cells can be accomplished by a variety of techniques, including, but not limited to calcium-phosphate-DNA co-precipitation, electroporation, microinjection, *Agrobacterium*-mediated transformation, liposome-mediated transformation, protoplast fusion or microprojectile bombardment (Christou, 1992; Sanford et al, 1993). The skilled artisan can refer to the literature for details and select suitable techniques for use in the methods of the present invention.

When *Agrobacterium* is used for plant cell transformation, a vector is introduced into the *Agrobacterium* host for homologous recombination with T-DNA or the Ti- or Ri-plasmid present in the *Agrobacterium* host. The Ti- or Ri-plasmid containing the T-DNA for recombination may be armed (capable of causing gall formation) or disarmed (incapable of causing gall formation), the latter being permissible, so long as the vir genes are present in the transformed *Agrobacterium* host. The armed plasmid can give a mixture of normal plant cells and gall.

In some instances where *Agrobacterium* is used as the vehicle for transforming host plant cells, the expression or transcription construct bordered by the T-DNA border region(s) is inserted into a broad host range vector capable of replication in *E. coli* and *Agrobacterium*, examples of which are described in the literature, for example pRK2 or derivatives thereof. See, for example, Ditta et al., 1980 and EPA 0 120 515. Alternatively, one may insert the sequences to be expressed in plant cells into a vector containing separate replication sequences, one of which stabilizes the vector in *E. coli*, and the other in *Agrobacterium*. See, for example, McBride and Summerfelt 1990, wherein the pRi-HRI (Jouanin, et al, 1985), origin of replication is utilized and provides for added stability of the plant expression vectors in host *Agrobacterium* cells.

Included with the expression construct and the T-DNA is one or more selectable marker coding sequences which allow for selection of transformed *Agrobacterium* and transformed plant cells. A number of antibiotic resistance markers have been developed for use with plant cells, these include genes inactivating antibiotics such as kanamycin, the aminoglycoside G418, hygromycin, or the like. The particular marker employed is not essential to this invention, with a particular marker preferred depending on the particular host and the manner of construction.

For *Agrobacterium*-mediated transformation of plant cells, explants are incubated with *Agrobacterium* for a time sufficient to result in infection, the bacteria killed, and the plant cells cultured in an appropriate selection medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of the recombinant protein produced by the plants.

There are a number of possible ways to obtain plant cells containing more than one expression construct. In one approach, plant cells are co-transformed with a first and second construct by inclusion of both expression constructs in a single transformation vector or by using separate vectors, one of which expresses desired genes. The second construct can be introduced into a plant that has already been transformed with the first expression construct, or alternatively, transformed plants, one having the first construct and one having the second construct, can be crossed to bring the constructs together in the same plant.

In a preferred embodiment, the plants used in the methods of the present invention are derived from members of the taxonomic family known as the Gramineae. This includes all members of the grass family of which the edible varieties are known as cereals. The cereals include a wide variety of species such as wheat (*Triticum* sps.), rice (*Otyza* sps.) barley (*Hordeum* sps.) oats, (*Avena* sps.) rye (*Secale* sps.), corn (maize) (*Zea* sps.) and millet (*Pennisettum* sps.). In practicing the present invention, preferred grains are rice, wheat, maize, barley, rye and triticale, and most preferred is rice.

In order to produce transgenic plants that express human blood protein in seeds, monocot plant cells or tissues derived from them are transformed with an expression vector comprising the coding sequence for a human blood protein. The transgenic plant cells are cultured in medium containing the appropriate selection agent to identify and select for plant cells which express the heterologous nucleic acid sequence. After plant cells that express the heterologous nucleic acid sequence are selected, whole plants are regenerated from the selected transgenic plant cells. Techniques for regenerating whole plants from transformed plant cells are generally known in the art.

Transgenic plant lines, e.g., rice, wheat, corn or barely, can be developed and genetic crosses carried out using conventional plant breeding techniques.

Transformed plant cells are screened for the ability to be cultured in selective media having a threshold concentration of a selective agent. Plant cells that grow on or in the selective media are typically transferred to a fresh supply of the same media and cultured again. The explants are then cultured under regeneration conditions to produce regenerated plant shoots. After shoots form, the shoots are transferred to a selective rooting medium to provide a complete plantlet. The plantlet may then be grown to provide seed, cuttings, or the like for propagating the transformed plants. The method provides for efficient transformation of plant cells and regeneration of transgenic plants, which can produce a recombinant human blood protein.

The expression of the recombinant human blood protein may be confirmed using standard analytical techniques such as Western blot, ELISA, PCR, HPLC, NMR, or mass spectroscopy, together with assays for a biological activity specific to the particular protein being expressed.

A purified blood protein recombinantly produced in a plant cell, preferably substantially free of contaminants of the host plant cell, and preferably comprising at least one plant glycosyl group is also provided by the invention. The plant glycosyl groups, while identifying that the blood protein was produced in a plant, does not significantly impair the biological activity of the blood protein in any of the applied therapeutic contexts (preferably less than 25% loss of activity, more preferably less than 10% loss of activity, as compared to a corresponding non-recombinant human blood protein). Typically, in accordance with some embodiments of the invention, the human blood protein constitutes at least about 0.5%, at least about 1.0% or at least about 2.0% of the total soluble protein in the seeds harvested from the transgenic plant. In a preferred embodiment, however, protein expression is much higher than previously reported, i.e., at least about 3.0%, which makes commercial production quite feasible. Advantageously, protein expression is at least about 5.0%, at least about 10%, at least about 15%, at least about 20%, at least about 30%, or even at least about 40% of total soluble protein.

The invention includes plant seed product prepared from the harvested seeds. Preferably, the human blood protein constitutes at least about 3.0% of the total soluble protein in the seed product, more preferably at least about 5.0%, and most preferably at least about 10.0%. As shown in the figures, the expression of human blood proteins in rice grains, represented by AAT, the three fibrinogen polypeptides and HSA represent at least about 10% of total soluble protein.

The present invention also provides compositions comprising human blood proteins produced recombinantly in the seeds of monocot plants, and methods of making such compositions. In practicing the invention, a human blood protein is produced in the seeds or grain of transgenic plants that express the nucleic acid coding sequence for the human blood protein. After expression, the blood protein may be provided to a patient in substantially unpurified form (i.e., at least 20% of the composition comprises plant material), or the blood protein may be isolated or purified from a product of the mature seed (e.g., flour, extract, malt or whole seed, etc.) and formulated for delivery to a patient.

Such compositions can comprise a formulation for the type of delivery intended. Delivery types can include, e.g. parenteral, enteric, inhalation, intranasal or topical delivery. Parenteral delivery can include, e.g. intravenous, intramuscular, or suppository. Enteric delivery can include, e.g. oral administration of a pill, capsule, or other formulation made with a non-nutritional pharmaceutically-acceptable excipient, or a composition with a nutrient from the transgenic plant, for example, in the grain extract in which the protein is made, or from a source other than the transgenic plant. Such nutrients include, for example, salts, saccharides, vitamins, minerals, amino acids, peptides, and proteins other than the human blood protein. Intranasal and inhalant delivery systems can include spray or aerosol in the nostrils or mouth. Topical delivery can include, e.g. creams, topical sprays, or salves. Preferably, the composition is substantially free of contaminants of the transgenic plant, preferably containing less than 20% plant material, more preferably less than 10%, and most preferably, less than 5%. The preferable route of administration is enteric, and preferably the composition is non-nutrititional.

The blood protein can be purified from the seed product by a mode including grinding, filtration, heat, pressure, salt extraction, evaporation, or chromatography.

The human blood proteins produced in accordance with the invention also include all variants thereof, whether allelic variants or synthetic variants. A "variant" human blood protein-encoding nucleic acid sequence may encode a variant human blood protein amino acid sequence that is altered by one or more amino acids from the native blood protein sequence, preferably at least one amino acid substitution, deletion or insertion. The nucleic acid substitution, insertion or deletion leading to the variant may occur at any residue within the sequence, as long as the encoded amino acid sequence maintains substantially the same biological activity of the native human blood protein. In another embodiment, the variant human blood protein nucleic acid sequence may encode the same polypeptide as the native sequence but, due to the degeneracy of the genetic code, the variant has a nucleic acid sequence altered by one or more bases from the native polynucleotide sequence.

The variant nucleic acid sequence may encode a variant amino acid sequence that contains a "conservative" substitution, wherein the substituted amino acid has structural or chemical properties similar to the amino acid which it replaces and physicochemical amino acid side chain properties and high substitution frequencies in homologous proteins found in nature (as determined, e.g., by a standard Dayhoff frequency exchange matrix or BLOSUM matrix). In addition, or alternatively, the variant nucleic acid sequence may encode a variant amino acid sequence containing a "non-conservative" substitution, wherein the substituted amino acid has dissimilar structural or chemical properties to the amino acid it replaces. Standard substitution classes include six classes of amino acids based on common side chain properties and highest frequency of substitution in homologous proteins in nature, as is generally known to those of skill in the art and may be employed to develop variant human blood protein-encoding nucleic acid sequences.

As will be understood by those of skill in the art, in some cases it may be advantageous to use a human blood protein-encoding nucleotide sequences possessing non-naturally occurring codons. Codons preferred by a particular eukaryotic host can be selected, for example, to increase the rate of human blood protein expression or to produce recombinant RNA transcripts having desirable properties, such as a longer half-life, than transcripts produced from naturally occurring sequence. As an example, it has been shown that codons for genes expressed in rice are rich in guanine (G) or cytosine (C) in the third codon position (Huang et al., 1990). Changing low G+C content to a high G+C content has been found to increase the expression levels of foreign protein genes in barley grains (Horvath et al., 2000). The blood protein encoding genes employed in the present invention were synthesized by Operon Technologies (Alameda, Calif.) based on the rice gene codon bias (Huang et al., 1990) along with the appropriate restriction sites for gene cloning. These 'codon-optimized' genes were linked to regulatory/secretion sequences for seed-directed monocot expression and these chimeric genes then inserted into the appropriate plant transformation vectors.

A human blood protein-encoding nucleotide sequence may be engineered in order to alter the human blood protein coding sequence for a variety of reasons, including but not limited to, alterations which modify the cloning, processing and/or expression of the human blood protein by a cell.

Heterologous nucleic acid constructs may include the coding sequence for a given human blood protein (i) in isolation; (ii) in combination with additional coding sequences; such as fusion protein or signal peptide, in which the human blood protein coding sequence is the dominant coding sequence; (iii) in combination with non-coding sequences, such as introns and control elements, such as promoter and terminator elements or 5' and/or 3' untranslated regions, effective for expression of the coding sequence in a suitable host; and/or (iv) in a vector or host environment in which the human blood protein coding sequence is a heterologous gene.

Depending upon the intended use, an expression construct may contain the nucleic acid sequence encoding the entire human blood protein, or a portion thereof. For example, where human blood protein sequences are used in constructs for use as a probe, it may be advantageous to prepare constructs containing only a particular portion of the human blood protein encoding sequence, for example a sequence which is discovered to encode a highly conserved human blood protein region.

The invention provides, in one embodiment, a seed composition containing a flour, extract, or malt obtained from mature monocot seeds and one or more seed-produced human blood proteins in unpurified form. Isolating the blood proteins from the flour can entail forming an extract composition by milling seeds to form a flour, extracting the flour with an aqueous buffered solution, and optionally, further treating the extract to partially concentrate the extract and/or remove unwanted components. In a preferred method, mature monocot seeds, such as rice seeds, are milled to a flour, and the flour then suspended in saline or in a buffer, such as Phosphate Buffered Saline ("PBS"), ammonium bicarbonate buffer, ammonium acetate buffer or Tris buffer. A volatile buffer or salt, such as ammonium bicarbonate or ammonium acetate may obviate the need for a salt-removing step, and thus simplify the extract processing method.

The flour suspension is incubated with shaking for a period typically between 30 minutes and 4 hours, at a temperature between 20-55° C. The resulting homogenate is clarified either by filtration or centrifugation. The clarified filtrate or supernatant may be further processed, for example by ultrafiltration or dialysis or both to remove contaminants such as lipids, sugars and salt. Finally, the material maybe dried, e.g., by lyophilization, to form a dry cake or powder. The extract combines advantages of high blood-protein yields, essentially limiting losses associated with protein purification.

In general, the protein once produced in a product of a mature seed can be further purified by standard methods known in the art, such as by filtration, affinity column, gel electrophoresis, and other such standard procedures. The purified protein can then be formulated as desired for delivery to a human patient. More than one protein can be combined for the therapeutic formulation. The protein may be purified and used in biomedical applications requiring a non-food administration of the protein.

The following examples illustrate but are not intended in any way to limit the invention.

EXAMPLE 1

Production of Transgenic Rice Encoding AAT and Fibrinogen Polypeptides

The basic procedures of particle bombardment-mediated rice transformation and plant regeneration were carried out as described by Huang et al., 2001. Rice variety TP309 seeds were dehusked, sterilized in 50% (v/v) commercial bleach for 25 min and washed with sterile water. The sterilized seeds were placed on rice callus induction medium (RCI) plates containing [N6 salts (Sigma), B5 vitamins (Sigma), 2 mg/l 2,4-D and 3% sucrose]. The rice seeds were incubated for 10 days to induce callus formation. Primary callus was dissected from the seeds and placed on RCI for 3 weeks.

This was done twice more to generate secondary and tertiary callus which was used for bombardment and continued subculture. A callus of 1-4 mm diameter was placed in a 4 cm circle on RCI with 0.3M mannitol 0.3M sorbitol for 5-24 hrs prior to bombardment. Microprojectile bombardment was carried out using the Biolistic PDC-1000/He system (Bio-Rad). The procedure requires 1.5 mg gold particles (60 ug/ml) coated with 2.5 ug DNA. DNA-coated gold particles were bombarded into rice calli with a He pressure of 1100 psi. After bombardment, the callus was allowed to recover for 48 hrs and then transferred to RCI with 30 mg/l hygromycin B for selection and incubated in the dark for 45 days at 26° C. Transformed calli were selected and transferred to RCI (minus 2,4-D) containing 5 mg/l ABA, 2 mg/l BAP, 1 mg/l NAA and 30 mg/l hygromycin B for 9-12 days. Transformed calli were transferred to regeneration medium consisting of RCI (minus 2,4-D), 3 mg/l BAP, and 0.5 mg/l NAA without hygromycin B and cultured under continuous lighting conditions for 2-4 weeks. Regenerated plantlets (1-3 cm high) were transferred to rooting medium whose concentration was half that of MS medium (Sigma) plus 1% sucrose and 0.05 mg/l NM. After 2 weeks on rooting medium, the plantlets developed roots and the shoots grew to about 10 cm. The plants were transferred to a 6.5×6.5 cm pots containing a mix of 50% commercial soil (Sunshine #1) and 50% soil from rice fields. The plants were covered by a plastic container to maintain nearly 100% humidity and grown under continuous light for 1 week. The transparent plastic cover was slowly shifted over a 1 day period to gradually reduce humidity and water and fertilizers added as necessary. When the transgenic R0 plants were approximately 20 cm in height, they were transferred to a greenhouse where they grew to maturity.

Individual R1 seed grains from the individual R0 regenerated plants were dissected into embryos and endosperms. Expression levels-of recombinant blood proteins (AAT and fibrinogen poypeptides) in the isolated rice endosperms were determined. Embryos from the individual R1 grains with high recombinant protein expression were sterilized in 50% bleach for 25 min and washed with sterile distilled water. Sterilized embryos were placed in a tissue culture tube containing ½ MS basal salts with the addition of 1% sucrose and 0.05 mg/l NAA. Embryos were germinated and plantlets having ~7 cm shoots and healthy root systems were obtained in about 2 weeks. Mature R1 plants were obtained as regenerants.

EXAMPLE 2

Production of Rice Extract Containing Recombinant Blood Proteins and its Use in Parenteral and Enteric Formulations General Procedure for Production of Rice Extract Transgenic rice containing heterologous polypeptides can be converted to rice extracts by either a dry milling or wet milling process. In the dry milling process, transgenic paddy rice seeds containing the heterologous polypeptides were dehusked with a dehusker. The rice was grounded into a fine flour though a dry milling process, for example, in one experiment, at speed 3 of a model 91 Kitchen Mill from K-TEC. Phosphate buffered saline ("PBS"), containing 0.135 N NaCl, 2.7 mM KCl, 10 mM $Na_2HPO_4$, 1.7 mM $KH_2PO_4$, at pH 7.4, with or without additional NaCl, such as 0.35 N NaCl, was added to the rice flour. In some experiments, approximately 10 ml of extraction buffer was used for each 1 g of flour. In other experiments, the initial flour/buffer ratio varied over a range such as 1 g/40 ml to 1 g/10 ml. The mixture was incubated at room temperature with gentle shaking for 1 hr. In other experiments, the incubation temperature was lower or higher, such as from about 22° C. to about 60° C., and the incubation time was longer or shorter, such as from about 10 minutes to about 24 hr. A Thermolyne VariMix platform mixer set at high speed was used to keep the particulates suspended.

Transgenic rice containing heterologous polypeptides can be converted to rice extracts by either a dry milling or wet milling process. In the dry milling process, transgenic paddy rice seeds containing the heterologous polypeptides were dehusked with a dehusker. The rice was grounded into a fine flour though a dry milling process, for example, in one experiment, at speed 3 of a model 91 Kitchen Mill from K-TEC. Phosphate buffered saline ("PBS"), containing 0.135 N NaCl, 2.7 mM KCl, 10 mM $Na_2HPO_4$, 1.7 mM $KH_2PO_4$, at pH 7.4, with or without additional NaCl, such as 0.35 N NaCl, was added to the rice flour. In some experiments, approximately 10 ml of extraction buffer was used for each 1 g of flour. In other experiments, the initial flour/buffer ratio varied over a range such as 1 g/40 ml to 1 g/10 ml. The mixture was incubated at room temperature with gentle shaking for 1 hr. In other experiments, the incubation temperature was lower or higher, such as from about 22° C. to about 60° C., and the incubation time was longer or shorter, such as from about 10 minutes to about 24 hr. A THERMOLYNE® VARIMIX™ platform mixer set at high speed was used to keep the particulates suspended.

The resulting homogenate was clarified either by filtration or centrifugation. For the filtration method, the mixture was allowed to settle for about 30 minutes at room temperature, after which the homogenate was collected and filtered. Filters in three different configurations were purchased from Pall Gemansciences and used. They were: a 3 μm pleated capsule, a 1.2 μm serum capsule and a Suporcap capsule 50 (0.2 μm). For centrifugation, a Beckman J2-HC centrifuge was used and the mixture was centrifuged at 30,000 g at 4° C. for about 1 hr. The supernatant was retained and the pellet discarded.

In one embodiment, the filtrate and supernatant were further processed, for example by ultra-filtration or dialysis or both to remove components such as lipids, sugars and salt.

The filtrate from the above filtration procedure, which is also called the clarified extract, was then concentrated using a spiral wound tangential flow filter operated in a batch recirculation mode. In one embodiment, PES (polyethersulfone) 3000-4000 molecular weight cutoff membranes were used for this step. These final concentrated extracts were held overnight in a cold room.

The concentrated extracts were next dried to a powder by lyophilization. The lyophilized material was scraped from the lyophilizer trays and combined into a plastic bag. The dry material was compressed by drawing a vacuum on the bag and then the material was blended and the particle size reduced by hand-kneading it through the plastic.

Rice extract can also be produced using a wet milling procedure. Transgenic paddy rice seeds containing recombinant human blood protein can be re-hydrated for a period of 0 to 288 hrs at 30° C. The rehydrated seeds are ground in PBS extraction buffer. The initial seed/buffer ratio can vary over a range such as 1 g/40 ml to 1 g/10 ml.

Over 20% human blood protein can be recovered from the wet milling process. The result of the wet milling becomes an initial extract that may be kept cold (4° C.) or stored frozen until use depending on the stability of the blood protein target. The processing of initial extract to obtain dried extract is the same as that described for dry milling in this section.

EXAMPLE 3

Concentration and Diafiltration of Recombinant Blood Protein and Control Rice Extracts The conditions used in concentration and diafiltration vary depending on volume, speed, cost, etc. These conditions are standard in the art based on the description herein. The frozen initial extract was thawed in the coldroom (about 2-8° C.) for six hours. The thawed material was clarified though a 0.45 µm filter and concentrated using a 5000 Nominal Molecular Weight Cutoff membrane of Polyethersultone.

90 ml of the filtrate of control extract was concentrated to 10 ml and additional 10 ml of deionized water can be added to the concentrated filtrate. The diluted filtrate can be diafiltrated one more time using water. The precipitate starts forming at 16 mS and increases as the ionic strength decreases. A solution of 1.0M ammonium bicarbonate was added to the retentate to add ionic strength. The haze decreases although does not disappear completely. The material was diafiltered multiple times, in one embodiment three times, with water and multiple times, in one embodiment three times, with 0.1 M ammonium bicarbonate. It was concentrated to 9 ml and the membrane is rinsed with 0.1 M ammonium bicarbonate. The concentrate was filtered through several 0.2 µm button filters. In one embodiment, 2.3 ml of the filtrate is lyophilized as is; 2.3 ml of the filtrate is diluted to 12 ml with deionized water and lyophilized, and 2.0 ml of the filtrate is diluted to 25 ml with deionized water and lyophilized. All the filtrates remained clear.

A total of 89 ml of the filtrate of recombinant protein extract was concentrated to 10 ml, and additional 10 ml of 0.1 M ammonium bicarbonate is added. The resulting mixture is concentrated back to 10 ml and another 10 ml of 0.1 M ammonium bicarbonate is added. The retentate starts to haze up. The material was diafiltered multiple times, in one embodiment three times, with 0.1 M ammonium bicarbonate. It was concentrated to 9 ml and the membrane is rinsed with 0.1 M ammonium bicarbonate. The concentrate was filtered through several 0.45 µm button filters. In one embodiment, 2.0 ml of the filtrate was lyophilized as is; 2.0 ml of the filtrate was diluted to 12 ml with deionized water where a haze formed, and lyophilized, and 2.0 ml of the filtrate was diluted to 12 ml with 0.1 M ammonium bicarbonate that remained clear, and lyophilized.

EXAMPLE 4

Comparison of Trial Extraction of Recombinant Protein Rice with PBS and Ammonium Bicarbonate The conditions used in concentration and diafiltration vary depending on volume, speed, cost, etc. These conditions are all standard in the art based on the description herein. Recombinant protein rice flour is mixed with extraction buffer at about 100 g/L for about 1 hour using a magnetic stir bar. In one 2 L beaker, the extraction buffer is PBS, pH 7.4 plus 0.35 M NaCl. In another 2 L beaker, the extraction buffer is 0.5 M ammonium bicarbonate. A 15 cm Buchner funnel is pre-coated with about 6 g of Cel-pure C300 before adding another 20 g of Cel-pure C300. The mixture is filtered at about 3-4 Hg. It is then washed twice with about 100 ml of respective extraction buffer. The extracted filtrate is collected and concentrated with ultrafiltration cartridges: 5K Regenerate Cellulose, 5K PES, and 1K Regenerated Cellulose. The concentrates are lyophilized and analyzed for recombinant blood protein activity contents. The ammonium bicarbonate and PBS, pH7.4 plus 0.35 M NaCl both extract approximately the same amount of rAAT. There is little loss of recombinant protein units in the permeate with any of the ultrafiltration units that were used.

Other extraction buffer can also be used to extract recombinant proteins expressed in transgenic rice grains, for example Tris buffer, ammonium acetate, depending on applications.

EXAMPLE 5

Production of Rice Extracts Containing Recombinant Blood Proteins

The conditions used in concentration and diafiltration vary depending on volume, speed, cost, etc. These conditions are all standard in the art based on the description herein. All equipment is soaked in hot 0.1M NaOH at a starting temperature of about 55° C. Rice flour is added to an about 250-500 gal stainless steel tank containing 0.5M ammonium bicarbonate in a ratio of 95-105 g/L. It is mixed for about 60-80 minutes at about 9° C.

12 plates of 36 inch filter press C300 were pre-coated with about 3-6 kg Cel-pure C300. About 19-26 g/L of Cel-pure is added to the extract and mixed thoroughly. The mixture is pressed at a pressure of about 22 psi at a flow rate of about 82 liters/minute. The filtrate is collected into a 250 gal stainless steel tank and washed with 0.5M ammonium bicarbonate. The press is blown dry. This process is carried out at about 10° C.

The 300 NMW cut-off membranes (Polysulfone), which had been cleaned and stored with 0.1M NaOH after control run is rinsed thoroughly with deionized water. The extract is concentrated and bumped to a 100 gal stainless steel tank. The membrane and the concentration tank were flushed with 0.1M ammonium bicarbonate to recover all remaining extract. The products were covered with plastic and left in the 100 gal tank overnight at room temperature. The concentrate is filtered through spiral wound 1 µm filter and into 5 gal poly container.

EXAMPLE 6

Blending of Rice Extract Containing Recombinant Proteins into Parenteral, Inhalant, Intranasal and Topical Formulations.

Recombinant blood proteins (such as AAT) can be highly purified grains from cereal grains for use in medical/pharmaceutical applications. A purification protocol for rice seed extract expressed human AAT has been developed [Huang et al, 2002], consisting of preparing a rice seed extract according to the above examples and further purifying the extract preparation using Con-A, DEAE and Octyl Sepharose chromatography respectively. AAT can be purified to greater than 90% homogeneity utilizing such a procedure [Huang et al, 2002]. Purified AAT can be utilized in potential pharma/ medical applications for the following indications: AAT augmentation/replacement therapy [Sandhaus, 1993; Hubbard et al, 1989], cystic fibrosis [McElvaney et al,1991; Allen, 1996], psoriasis, panniculitis and cutaneous vasculitis [O'Riordan et al, 1997; Dowd et al, 1995] and pulmonary inflammation [Bingle and Tetley, 1996]. For some of these indications, purified AAT protein preparations can be administered via intravenous (iv) methods in 0.09% saline solution. Alternatively, the saline solution solution could be buffered with serum albumen at 0.5% or some other pharmacologically acceptable protein carrier molecule. AAT dosages are usually around 60 mg/kg. For aerosol delivery, an aerosol generating system can be employed utilizing a compressed air driven nebulizer selected on the basis of the basis of its ability to generate an aerosol with droplets of the optimum size (<3 um in aerodynamic diameter) for deposition in the lower respiratory tract [Hubbard et al, 1989]. Again proteins can either be suspended in sterile water or a buffered saline solution containing a pharmacologically acceptable protein carrier. Alternatively, a dried protein powder containing the purified protein component could be utilized as the dispersal agent and this could be an a rice based extract where the AAT component is greater but not less then 50% by weight.

In another case, recombinant rice expressed and extracted human blood proteins such as AAT and fibrinogen can be employed topically. The use of fibrin sealants/bandages has been a widely accepted used by the medical community. Fibrin sealants are effective hemostatic agents [Mankad and Codispoti, 2001], a means for achieving tissue adhesion, preventing fluid accumulation and promotion of wound healing [Spotnitz, 2001]. Fibrin sealants can also be used as a means of slowly releasing medications, including antibiotics, growth factors and other agents [Spotnitz, 1997]. Rice expressed fibrinogen can also provide a potential low cost and animal virus free source for these indications.

References

1. Allen, E. D. (1996). Opportunities for the use of aerosolized α1-antitrypsin for the treatment of cystic fibrosis. *CHEST* 110: 256S-260S.
2. Ausubel F. M. et al., CURRENT PROTOCOLS IN MOLECULAR BIOLOGY, John Wiley & Sons, New York, N.Y., 1993.
3. Beatty, K., Beath, J. and Travis, J. (1980). Kinetics of association of serine proteinase with native and oxidized α-1-proteinase inhibitor and α-1-antichymotrypsin. *Jour Biol Chem* 255: 3931-34.
4. Bednarek, S. Y. and Raikel, N. V. (1992). Intracellular trafficking of secretory proteins. *Plant Mol Biol* 20: 133-50.
5. Bhagavan, N. V. (2002). "Biochemistry of Hemostatis" in Medical Biochemistry, Academic Press Inc, Harcourt Inc, Orlando, Fla.
6. Bhagavan, N. V. (2002). "Molecular Immunology" in Medical Biochemistry, Academic Press Inc, Harcourt Inc, Orlando, Fla.
7. Bingle, L. and Tetley, T. D. (1996). Secretory leukoprotease inhibitor; partnering α1-proteinase inhibitor to combat pulmonary inflammation. *Thorax* 51:1273-4.
8. Brennan, S. O., Owen, M. C., Boswell, D. R., Lewis, J. H. and Carrell, R. W. (1984). Circulating proalbumin associated with a variant proteinase inhibitor. *Biochem Biophys Acta* 802: 24-28.
9. Brown, J. H., Volkmann, N., Jun, G., Henschen-Edman, A. H. and Cohen, C. (2000). The crystal structure of modified bovine fibrinogen. *Proc Natl Acad Sci* 97: 85-90.
10. Carrell, R. W., Jeppsson, J. O., Vaughan, L., Brennen, S., Owen, M. C. and Boswell, D. R. (1981). Human α-1-antitrypsin: Carbohydrate attachment and sequence homology. *FEBS Lett* 135: 301-3.
11. Carrell, R. W., Jeppson, J. O., Laurrell, C. B., Brennan, S. O., Owen, M. C., Vaughan, L. and Boswell, D. R. (1982). Structure and variation of human alpha-1-antitrypsin. *Nature* 298: 329-34.
12. Chrispeels, M. J. (1991). Sorting proteins in the secretory system. *Annu Rev Plant Physiol Plant Mol Biol* 42: 21-53.
13. Chrispeels, M. J. and Raikhel, N. V. (1992). Short peptide domains target proteins to plant vacuoles. *Cell* 68: 613-16.
14. Christou, P. (1992). Genetic transformation of crop plants using microprojectile bombardment. *Plant Jour* 2: 275-281.
15. Daniell, H., Streatfield, S. J. and Wycoff, K. (2001). Medical molecular farming: production of antibodies, biopharmaceuticals and edible vaccines in plants. *TRENDS Plant Sci* 6: 219-226.
16. Davidson L. A. and Lonnerdal, B. (1987). Persistence of human milk proteins in the breast-fed infant. *Act Pediatric Scand* 76: 733-40.
17. Ditta, G., Stansfield, S., Corbin, D. and Helinski, D. R. (1980). Broad host ramge DNA cloning system from gram-negative bacteria: Construcyionof a gene bank from *Rhizobium meliloti. Proc Natl Acad Sci USA* 77: 7347-51.
18. Dowd, S. K., Rodgers, G. C. and Callen, J. P. (1995). Effective treqatment with α1 -protease inhibitor of chronic cutaneous vasculitis associated with α1-antitrypsin deficiency. *Jour Am Acad Dermatol* 33: 913-6.
19. Eriksson, S. (1964). *Acta Medic Scand* 175: 197-205.
20. Everse, S. J., Spraggon, G., Veerapandian, L. and Doolittle, R. F. (1999) Conformational changes in fragments D and doubl-D from human fibrinogen upon binding the peptide ligan Gly-His-Pro-amide. *Biochemistry* 38: 2941-2946.
21. Friezner-Degen S. J., MacGillivray, R. T. A. and Davie, E. W. (1983). Characterization of the complementary deoxyribonucleic acid and gene coding for human prothrombin. *Biochemistry* 22: 2087-97.
22. Holmberg, N., Gosta, L, Bailey, J. E. and Bulow, L. (1997). Transgenic tobacco expressing Vitreoscilla hemoglobin exhibits enhanced growth and altered metabolite production. *Nature Biotech* 15: 244-7.
23. Hiatt, A., Cafferkey, R. and Bowdish, K. (1989). Production of antibodies in transgenic plants. *Nature* 342: 76-8.
24. Hiatt, A. and Ma, J. K. C. (1992). Monoclonal antibody engineering in plants. *FEBS Letters* 307: 71-5.
25. Horvath, H., Huang, J., Wong. O., Kohl E., Okita, T., Kannangara, C. G. and vonWettstein, D. (2000). The production of recombinant proteins in transgenic barley grains. *Proc Natl Acad Sci USA* 97: 1914-19.
26. Huang, N., Simmons, C. R. and Rodriguez, R. L. (1990). Codon usage patterns in plant genes. *J CAASS* 1: 73-86.
27. Huang, N., Wu, I., Nandi, S., Bowman, E., Huang, J., Sutliff, T. and Rodriguez, R. L. (2001). The tissue-specific activity of a rice B-glucanase promoter (Gns9) is used to select rice transformants. *Plant Sci* 161: 589-95.
28. Huang, J., Sutliff, T. D., Wu, L., Nandi, S., Benge, K., Terashima, M., Ralston, A. H., Drohan, W., Huang, N. and Rodriguez, R. L. (2001). Expression and purification of functional human α-1-antitrypsin from cultured plant cells. *Biotechnol Prog* 17: 126-33.
29. Hubbard, R. C., McElvaney, N. G., Sellers, S. E., Healy, J. T., Czerski, D. B. and Crystal, R. G. (1989). Recombinant DNA-produced α1-antitrypsin administered by aerosol augments lower respiratory tract antineutrophil elastase defenses in individuals with α1-antitrypsin deficiency. *Jour Clinical Invest* 84: 1349-54.
30. Jouanin, L., Vilaine, F., d'Enfert, C. and Casse-Delbart, F. (1985). Localization and restriction maps of the replication origin regions of the plasmids of *Agrobacterium rhizogenes* strain A₄. *Mol Gen Genet* 201: 370-4.
31. Judah, J. D., Gamble, M. and Steadman, J. H. (1973). Biosynthesis of serum albumin in rat liver, evidence for the exsistance of 'proalbumin'. *Biochem J* 134: 1083-91.
32. Kurachi, K., Chandra, T., Degen, S. J., White, T. T., Marchioro, T. L., Woo, S. L. and Davie, E. W. (1981). Cloning and sequence of a cDNA coding for α-1-antitryspin. *Proc Natl Acad Sci* 78: 6826-30.
33. Ma, J. K. C., Hiatt, A., Hein, M., Vine, N. D., Wang, F., Stabila, P., van Dolleweerd, C., Mostov, K. and Lehner, T. (1995). Generation and assembly of Secretory Antibodies in plants. *Science* 268: 716-9.
34. Madrazo, J., Bzrown, J. H., Litvinovich, S., Dominguez, R., Yakovlev, S., Medved, L., and Cohen, C. (2001) Crystal structure of the central region of bovine fibrinogen E5 fragment at 1.4 A resolution. *Proc Natl Acad Sci* 98: 11967-72.
35. Mankad, P. S. and Codispoti, M. (2001). The role of fibrin sealants in hemostasis. *Amer Jour Surg* 182: 21S-28S.
36. McBride, K. E. and Summerfelt, K. R. (1990). Improved binary vectors for *Agrobacterium* mediated plant transformation. *Plant Mol Biol* 14: 269-76.
37. McElvaney, N. G., Hubbard, R. C., Birrer, P., Chernick, M. S., Caplan, D. B., Frank, M. M. and Crystal, R. G. (1991). Aerosol α1-antitrypsin treatment for cystic fibrosis. *The Lancet* 337: 392-4.
38. McGilligan, K. M., Thomas, D. W. and Eckert, C. D. (1987). Alpha-1-antitrypsin concentration in human milk. *Pediatr Res* 22: 268-70.
39. O'Riordan, K., Blei, A., Rao, M. S. and Abecassis, M. (1997). α1-antitrypsin deficiency-associated panniculitis. *Transplant* 63: 480-2.
40. Peters, T. J. (1996). All About Albumin: Biochemistry, genetics and medical applications. Academic Press Inc, Harcourt Brace & Company, Orlando, Fla.
41. Rabiet, M. J., Blashill, A., Furie, B. and Furie, B. C. (1986). Prothrombin fragment 1*2*3; a major product of prothrombin activation in human plasma. *Jour Biol Chem* 261: 13210-15.
42. Rosenberg, J. S., Beeler, D. L. and Rosenberg, R. D. (1975). Activation of human prothrombin by highly purified human factors V and $X_a$ in the presence of human antithrombin. *Jour Biol Chem* 250: 1607-17.
43. Travis, J. and Salvesen, G. S. (1983). Human plasma proteinase inhibitors. *Annu Rev Biochem* 655-709.
44. Sambrook J. et al., MOLECULAR CLONING: A LABORATORY MANUAL (Second Edition), Cold Spring arbor Press, Plainview, N.Y., 1989.
45. Sandhaus, R. A. (1993). "Alpha-1-antitrypsin augmentation therapy" in Proteases, Protease Inhibitors and Protease-Derived Peptides, Birkhauser Verlag, Basel, pp 97-102 Sanford, J., Smith, F. D. and Russell, J. A. (1993). Optimizing the biolistic process for different biological applications. *Meth Enzymol* 217: 83-509.
46. Shieh, M. W., Wessler, S. R. and Raikel, N. V. (1993). Nuclear targeting of the maize R protein requires two nuclear localization sequences. *Plant Physiol* 101: 353-61.
47. Sijmons, P. C., Dekker, B. M., Schrammeijer, B., Verwoerd, T. C., van den Elzen, P. J. M. and Hoekema, A. (1990). Production of correctly processed human serum albumin in transgenic plants. *Bio/Technology* 8: 217-21.
48. Smeekens, S., Bauerle, C., Hageman, J., Keegstra, K. and Weisbeek, P. (1986) The role of the transit peptide in the routing of precursors towards different chloroplast compartments. *Cell* 46: 365-76.
49. Spotnitz, W. D. (1997). New developments in the use of fibrin sealants: a surgeon's perspective. *Jour Long Term Effects Med Implants* 7: 243-53.
50. Spotnitz, W. D. (2001). Commercial fibrin sealants in surgical care. *Amer Jour Surg* 182: 8S-14S. Vine, N. D., Drake, P., Hiatt, A. and Ma, J. K. C. (2001). Assembly and plasma membrane targeting of recombinant immunoglobin chains in plants with a murine immunoglobin transmembrane sequence. *Plant Molec Biol* 45: 159-67.
51. Tietz, N. W. (1995). Clinical Guide to Laboratory Tests, W. B. Saunders, Philadelphia.
52. Varagona, M. J., Schmidt, R. J. and Raikhel, N. V. (1992). Nuclear localization signals required for nuclear targeting of the maize regulatory protein, Opaque-2. *Plant Cell* 4: 1213-27.
53. Vitale, A. and Chrispeels, M. J. (1992). Sorting of proteins to the vacuoles of plant cells. *BioEssays* 14: 151-60.
54. Wassmen, C. C., Reiss, B., Bartlett, S. G. and Bohnert, H. J. (1986). The importance of the transit peptides and the transported protein for protein import into chloroplasts. *Mol Gen Genet* 205: 446-53.
55. Weeke, B. and Krasinikoff (1971). A polynomial expression for the serum concentrations of 21 serum proteins from 1 to 93 years of age in normal males and females. *Protein Biol Fluids* 18: 173-9.
56. Yakovlev, S., Litvinovich, S., Loukinov, D. and Medved, L. (2000). Role of the beta-strand in the central domain of fibrinogen gamma module. *Biochemistry* 39: 15721-9.
57. Yang, Z., Mochalkin, I., Veerapandian, L., Riley, M. and Doolittle, R. F. (2000) Crystal structure of native chicken fibrinogen at 5.5 A resolution. *Proc Natl Acad Sci* 97: 3907-12.

All publications cited herein are expressly incorporated herein by reference.

What is claimed is:

1. A method of producing human serum albumin (HSA) in monocot plant seeds, comprising the steps of:
   (a) transforming a monocot plant cell with a chimeric gene comprising
      (i) a promoter from the gene of a maturation-specific monocot plant storage protein, wherein the promoter comprises SEQ ID NO.:8,
      (ii) a first DNA sequence, operably linked to the promoter, encoding a signal sequence, and
      (iii) a second DNA sequence, linked in translation frame with the first DNA sequence, encoding HSA, wherein the first DNA sequence and the second DNA sequence together encode a fusion protein comprising an N-terminal signal sequence and the HSA;
   (b) growing a monocot plant from the transformed monocot plant cell for a time sufficient to produce seeds containing the HSA; and
   (c) harvesting the seeds from the plant,
   wherein the HSA constitutes at least about 10% of the total soluble protein in the harvested seeds.

2. The method of claim 1, further comprising purifying the HSA from the harvested seeds.

* * * * *

SEQUENCE LISTING

<160> NUMBER OF SEQ ID NOS: 21

<210> SEQ ID NO 1
<211> LENGTH: 1878
<212> TYPE: DNA
<213> ORGANISM: Artificial Sequence
<220> FEATURE:
<223> OTHER INFORMATION: Description of Artificial Sequence:
    Codon-optimized fibrinogen a-polypeptide coding sequence

```
<400> SEQUENCE: 1
gccgactccg gcgagggcga cttcctcgcc gagggcggcg gcgtccgggg gccgcgcgtc      60
gtcgagcggc accagtcggc ctgcaaggac tccgactggc cgttctgctc ggacgaggac     120
tggaactaca agtgcccctc cggctgccgc atgaaggggc tgatcgacga ggtcaaccag     180
gacttcacca accgcatcaa caagctcaag aactcgctgt tcgagtacca agaacaac      240 aaggactccc actccctcac gaccaacatc atggagatcc tgcgcggcga cttctcctcc     300 gcgacaacc gcgacaacac ctacaaccgc gtctcggagg acctccgctc ccgcatcgag      360
gtcctgaagc ggaaggtgat cgagaaggtc agcacatcc agctcctcca aaagaacgtc     420
cgcgcccagc tcgtggacat gaagcgcctg gaggtggaca tcgacatcaa gatccggtcg     480
tgccgcggca gctgctcccg cgccctcgcc gcgaggtgg acctcaagga ctacgaggac      540
cagcagaagc agctggagca ggtcatcgcc aaggacctcc tcccgagccg cgaccggcag     600
cacctcccac tgatcaagat gaagccgtg ccagacctgg tccccggcaa cttcaagagc      660
cagctccaga aggtcccgcc ggagtggaag gccctcacgg acatgcccca aatgcgcatg     720
gagctggagc gccccggcgg caacgagatc acgcgggggcg gctccacctc gtacggcacg     780
ggctccgaga ccgagagccc ccgcaacccc tcctccgccg gctcgtggaa ctcggggtcc      840 agcgccccg gttccacggg caaccgcaac cccggctcgt ccggcaccgg tggcaccgcc     900
acgtggaagc aggtagctc ggggccgggc agcaccggca gctggaactc cggcagcagc      960
ggcaccggct cgacgggcaa ccagaacccg ggcagccccc gccccggctc cacggggacc    1020
tggaacccag gctcctccga gcggggggtcc gccggccact ggacgagcga gagctcggtg    1080
tcgggctcga ccggccagtg gcactcggaa tccggcagct tccggccaga ctcccccggc    1140
agcggcaacg cccggccgaa caacccagac tgggggcacct tcgaggaggt ctccggtaac    1200 gtgagcccg gcacgcgccg ggagtaccac acggagaagc tggtgacgtc gaagggcgac    1260
aaggagctcc ggaccggcaa ggagaaggtg acctccggct cgaccaccac cacccggcgg    1320
tcctgctcga agaccgtgac gaagaccgtc atcggtccgg acggccacaa ggaggtcacc    1380
aaggaggtgg tcaccagcga ggacggctcg gactgcccgg aggccatgga cctgggcacc    1440
ctcagcggca tcggcacgct ggacggcttc cgccaccggc acccggacga ggccgccttc    1500
ttcgacaccg ctagcaccgg caagaccttc cccggtttct tctcgccgat gctcggcgag    1560
ttcgtgtccg agacggagag ccggggcagc gagagtggca tcttcaccaa caccaaggaa    1620
tcctcctcgc accacccagg tatcgcggag ttcccgagcc ggggggaagtc ctcctcctac    1680 tccaagcagt tcaccagctc cacctcctac aaccggggcg acagcacgtt cgagagcaag    1740
agctacaaga tggccgacga ggccggttcc gaggccgacc acgagggcac ccactcgacg    1800
aagcgcgggc acgccaagtc gcgcccagtg cgcgggatcc acacgtcccc gcgtcgcaag    1860
cccagcctgt ccccgtga                                                   1878

<210> SEQ ID NO 2
<211> LENGTH: 1386
<212> TYPE: DNA
<213> ORGANISM: Artificial Sequence
<220> FEATURE:
<223> OTHER INFORMATION: Description of Artificial Sequence:
      Codon-optimized fibrinogen B-polypeptide coding sequence

<400> SEQUENCE: 2
caaggggtga acgacaacga ggagggtttc ttctccgccc gcggccaccg cccgctggac      60
```

```
aagaagcgcg aggaggcccc gagcctgcgc cccgcgcccc ccccatctc cggcggcggc      120 taccgggccc ggccggcaaa ggcggcggca acgcagaaga aggtcgagcg gaaggccccg      180
gacgccggcg gctgcctgca cgcggacccg gacctcggcg tcctgtgccc aacgggtgc       240 cagctccaag aggcgctcct ccaacaggag cgccccatcc ggaactccgt agacgagctg      300
aacaacaacg tggaggcagt gagccagacc tcctcgtcca gcttccagta catgtacctc      360
ctcaaggacc tctggcagaa gcggcaaaag caggtgaagg acaacgagaa cgtggtgaac      420
gagtacagct ccgagctcga aaagcaccag ctgtacatcg acgagaccgt gaactcgaac      480
atccccacga acctccgcgt cctgcgctcg atcctggaga acctccggag caagatccag      540
aagctagaat ccgacgtgtc ggcccagatg gagtattgcc ggaccccgtg caccgtcagc      600
tgcaacatcc cggtggtcag cggcaaggag tgcgaggaga tcatccgcaa gggcggcgag      660
accagcgaga tgtacctcat ccaacccgat tcctccgtca agccataccg ggtgtactgc      720
gacatgaaca cggagaacgg cggtggacc gtgatccaga accgccagga cggctccgtg       780
gacttcggcc gcaagtggga cccgtacaag cagggcttcg gcaacgtggc cacgaacacg      840
gacgggaaga actactgcgg gctccccggc gaatactggc tgggcaacga caagatctcc      900
cagctgaccc gcatgggccc caccgagctg ctcatcgaga tggaggactg gaagggcgac      960
aaggtgaagg cccactacgg ggggcttcacg gtgcagaacg aggcgaacaa gtaccaaatc     1020
tcggtgaaca agtaccgcgg caccgctggg aacgcgctca tggacggcgc gagccagctg     1080
atgggcgaga accgcaccat gaccatccac aacggcatgt tcttcagcac ctacgaccgc     1140
gacaacgacg ggtggctcac gagcgacccc cggaagcagt gctcgaagga ggacggcggc     1200
ggctggtggt acaaccgctg ccacgcggca aaccccaacg gtcgctacta ctggggcggt     1260
cagtacacgt gggacatggc gaagcacggc accgacgacg gcgtcgtctg gatgaactgg     1320
aagggctcgt ggtacagcat gcggaagatg tccatgaaga tccgccccctt cttcccccag    1380 cagtga                                                                1386
```

<210> SEQ ID NO 3
<211> LENGTH: 1236
<212> TYPE: DNA
<213> ORGANISM: Artificial Sequence
<220> FEATURE:
<223> OTHER INFORMATION: Description of Artificial Sequence:
      Codon-optimized fibrinogen γ-polypeptide encoding sequence

<400> SEQUENCE: 3

```
tacgtcgcca cccgggacaa ctgctgcatc ctggacgagc ggttcgggag ctactgccca       60
accacctgcg gcatcgccga cttcctgtcc acgtaccaga cgaaggtgga caaggacctc      120
cagtccctgg aggacatcct ccaccaggtg gagaacaaga cgtcggaggt caagcagctc      180
atcaaggcca tccagctcac ctacaacccg gacgaatcgt ccaagcccaa catgatcgac      240
gccgccaccc tcaagtcgcg gaagatgctg gaggagatca tgaagtacga ggcgtccatc      300
ctcacccacg actcctccat ccgctacctc caggagatct acaactccaa caaccaaaag      360
atcgtcaacc tcaaggagaa ggtcgcccag ctggaggcgc aatgccagga gccctgcaag      420
gacacggtgc aaatccacga catcacgggg aaggactgcc aagacatcgc caacaagggc      480
gccaagcaga gcgggctcta cttcatcaag ccctcaagg cgaaccagca gttcctggtc       540
tactgcgaga tcgacggctc gggcaacggc tggaccgtct ccagaagcg cctcgacggc       600 tccgtggact tcaagaagaa ctggatccaa tacaaggagg gcttcggcca cctctccccc      660
```

-continued

| | |
|---|---|
| accggcacga cggagttctg gctgggcaac gagaagatcc acctcatctc cacgcagagc | 720 |
| gcgatcccat acgccctccg ggtggagctg gaggactgga acggccgcac cagcaccgcg | 780 |
| gactacgcaa tgttcaaggt gggcccagag gcggacaagt accggctgac ctacgcctac | 840 |
| ttcgcgggcg gggacgcggg ggacgccttc gacgggttcg acttcggtga cgacccaagc | 900 |
| gacaagttct tcacgtccca caacggtatg cagttcagca cgtgggacaa cgacaacgac | 960 |
| aagttcgagg gtaactgcgc ggagcaggac ggcagcggct ggtggatgaa caagtgccac | 1020 |
| gcgggccacc tcaacggcgt ctactaccag ggcgggacct acagcaaggc atccacgcca | 1080 |
| aacgggtacg caacggtat catctgggcc acgtggaaga cgcgctggta cagcatgaag | 1140 |
| aagaccacca tgaagatcat cccgttcaac cggctgacca tcggtgaggg ccagcagcac | 1200 |
| cacctcggcg gggccaagca ggcgggcgac gtgtga | 1236 |

<210> SEQ ID NO 4
<211> LENGTH: 1748
<212> TYPE: DNA
<213> ORGANISM: Homo sapiens

<400> SEQUENCE: 4

| | |
|---|---|
| gatgcacaca agagtgaggt tgctcatcgg tttaaagatt tgggagaaga aaatttcaaa | 60 |
| gccttggtgt tgattgcctt tgctcagtat cttcagcagt gtccatttga agatcatgta | 120 |
| aaattagtga atgaagtaac tgaatttgca aaaacatgtg ttgctgatga gtcagctgaa | 180 |
| aattgtgaca aatcacttca taccttttt ggagacaaat tatgcacagt tgcaactctt | 240 |
| cgtgaaacct atggtgaaat ggctgactgc tgtgcaaaac aagaacctga gagaaatgaa | 300 |
| tgcttcttgc aacacaaaga tgacaaccca aacctccccc gattggtgag accagaggtt | 360 |
| gatgtgatgt gcactgcttt tcatgacaat gaagagacat ttttgaaaaa atacttatat | 420 |
| gaaattgcca aagacatcc ttacttttat gccccggaac tccttttctt tgctaaaagg | 480 |
| tataaagctg cttttacaga atgttgccaa gctgctgata agctgcctg cctgttgcca | 540 |
| aagctcgatg aacttcggga tgaagggaag gcttcgtctg ccaaacagag actcaagtgt | 600 |
| gccagtctcc aaaaatttgg agaaagagct ttcaaagcat gggcagtagc tcgcctgagc | 660 |
| cagagatttc ccaaagctga gtttgcagaa gtttccaagt tagtgacaga tcttaccaaa | 720 |
| gtccacacgg aatgctgcca tggagatctg cttgaatgtg ctgatgacag ggcggacctt | 780 |
| gccaagtata tctgtgaaaa tcaagattcg atctccagta aactgaagga atgctgtgaa | 840 |
| aaacctctgt ggaaaaatc ccactgcatt gccgaagtgg aaaatgatga gatgcctgct | 900 |
| gacttgcctt cattagctgc tgattttgtt gaaagtaagg atgtttgcaa aaactatgct | 960 |
| gaggcaaagg atgtcttcct gggcatgttt ttttatgaat atgcaagaag gcatcctgat | 1020 |
| tactctgtcg tgctgctgct gagacttgcc aagacatatg aaaccactct agagaagtgc | 1080 |
| tgtgccgctg cagatcctca tgaatgctat gccaaagtgt tcgatgaatt taaacctctt | 1140 |
| gtggaagagc tcagaatttt aatcaaacaa aattgtgagc tttttgagca gcttggagag | 1200 |
| tacaaattcc agaatgcgct attagttcgt tacaccaaga agtaccccca agtgtcaact | 1260 |
| ccaactcttg tagaggtctc aagaaaccta ggaaaagtgg gcagcaaatg ttgtaaacat | 1320 |
| cctgaagcaa aaagaatgcc ctgtgcagaa gactatctat ccgtggtcct gaaccagtta | 1380 |
| tgtgtgttgc atgagaaaac gccagtaagt gacagagtca ccaaatgctg cacagaatcc | 1440 |
| ttggtgaaca ggcgaccatg cttttcagct ctggaagtcg atgaaacata cgttcccaaa | 1500 |
| gagtttaatg ctgaaacatt caccttccat gcagatatat gcacactttc tgagaaggag | 1560 |

-continued

| agacaaatca agaaacaaac tgcacttgtt gagcttgtga caaggcaaca aaagagcaac | 1620 |
| tgaaagctgt tatggatgat ttcgcagctt ttgtagagaa gtgctgcaag gctgacgata | 1680 |
| aggagacctg ctttgccgag gagggtaaaa aacttgttgc tgcaagtcaa gctgccttag | 1740 |
| gcttataa | 1748 |

<210> SEQ ID NO 5
<211> LENGTH: 1185
<212> TYPE: DNA
<213> ORGANISM: Artificial Sequence
<220> FEATURE:
<223> OTHER INFORMATION: Description of Artificial Sequence: Codon
      optimized alpha-1-antitrypsin coding sequence

<400> SEQUENCE: 5

| gaggacccgc agggcgacgc cgcccagaag accgacacca gccaccacga ccaggaccac | 60 |
| ccgacgttca acaagatcac cccgaatttg gccgaattcg ccttcagcct gtaccgccag | 120 |
| ctcgcgcacc agtccaactc caccaacatc ttcttcagcc cggtgagcat cgccaccgcc | 180 |
| ttcgccatgc tgtccctggg taccaaggcg acacccacg acgagatcct cgaagggctg | 240 |
| aacttcaacc tgacggagat cccggaggcg cagatccacg agggcttcca ggagctgctc | 300 |
| aggacgctca accagccgga ctcccagctc cagctcacca ccggcaacgg gctcttcctg | 360 |
| tccgagggcc tcaagctcgt cgataagttc ctggaggacg tgaagaagct ctaccactcc | 420 |
| gaggcgttca ccgtcaactt cggggacacc gaggaggcca agaagcagat caacgactac | 480 |
| gtcgagaagg ggacccaggg caagatcgtg gacctggtca aggaattgga cagggacacc | 540 |
| gtcttcgcgc tcgtcaacta catcttcttc aagggcaagt gggagcgccc gttcgaggtg | 600 |
| aaggacaccg aggaggagga cttccacgtc gaccaggtca ccaccgtcaa ggtcccgatg | 660 |
| atgaagaggc tcggcatgtt caacatccag cactgcaaga agctctccag ctgggtgctc | 720 |
| ctcatgaagt acctggggaa cgccaccgcc atcttcttcc tgccggacga gggcaagctc | 780 |
| cagcacctgg agaacgagct gacgcacgac atcatcacga gttcctgga gaacgaggac | 840 |
| aggcgctccg ctagcctcca cctcccgaag ctgagcatca ccggcacgta cgacctgaag | 900 |
| agcgtgctgg ccagctggg catcacgaag gtcttcagca acggcgcgga cctctccggc | 960 |
| gtgacggagg aggcccccct gaagctctcc aaggccgtgc acaaggcggt gctcacgatc | 1020 |
| gacgagaagg ggacggaagc tgccggggcc atgttcctgg aggccatccc cgtgtccatc | 1080 |
| ccgcccgagg tcaagttcaa caagcccttc gtcttcctga tgatcgagca gaacacgaag | 1140 |
| agcccccctct tcatggggaa ggtcgtcaac cccacgcaga agtga | 1185 |

<210> SEQ ID NO 6
<211> LENGTH: 786
<212> TYPE: DNA
<213> ORGANISM: Oryza sp.

<400> SEQUENCE: 6

| catgagtaat gtgtgagcat tatgggacca cgaaataaaa agaacatttt gatgagtcgt | 60 |
| gtatcctcga tgagcctcaa aagttctctc accccggata agaaacccctt aagcaatgtg | 120 |
| caaagtttgc attctccact gacataatgc aaaataagat atcatcgatg acatagcaac | 180 |
| tcatgcatca tatcatgcct ctctcaacct attcattcct actcatctac ataagtatct | 240 |
| tcagctaaat gttagaacat aaacccataa gtcacgtttg atgagtatta ggcgtgacac | 300 |
| atgacaaatc acagactcaa gcaagataaa gcaaaatgat gtgtacataa aactccagag | 360 |

```
ctatatgtca tattgcaaaa agaggagagc ttataagaca aggcatgact cacaaaaatt     420
cacttgcctt tcgtgtcaaa agaggaggg ctttacatta tccatgtcat attgcaaaag     480
aaagagagaa agaacaacac aatgctgcgt caattataca tatctgtatg tccatcatta   540
ttcatccacc tttcgtgtac cacacttcat atatcataag agtcacttca cgtctggaca   600
ttaacaaact ctatcttaac atttagatgc aagagccttt atctcactat aaatgcacga   660
tgatttctca ttgtttctca caaaaagcgg ccgcttcatt agtcctacaa caacatggca   720
tccataaatc gccccatagt tttcttcaca gtttgcttgt tcctcttgtg cgatggctcc   780
ctagcc                                                                786

<210> SEQ ID NO 7
<211> LENGTH: 1055
<212> TYPE: DNA
<213> ORGANISM: Oryza sp.

<400> SEQUENCE: 7
ctgcagggag gagaggggag agatggtgag agaggaggaa gaagaggagg ggtgacaatg    60
atatgtgggg catgtgggca cccaattttt taattcattc ttttgttgaa actgacatgt   120
gggtcccatg agatttatta ttttcggat cgaatcgcca cgtaagcgct acgtcaatgc    180
tacgtcagat gaagaccgag tcaaattagc cacgtaagcg ccacgtcagc caaaaccacc   240
atccaaaccg ccgagggacc tcatctgcac tggttttgat agttgaggga cccgttgtat   300
ctggtttttc gattgaagga cgaaaatcaa atttgttgac aagttaaggg accttaaatg   360
aacttattcc atttcaaaat attctgtgag ccatatatac cgtgggcttc caatcctcct   420
caaattaaag ggcctttttta aaatagataa ttgccttctt tcagtcaccc ataaaagtac   480
aaaactacta ccaacaagca acatgcgcag ttacacacat tttctgcaca tttccgccac   540
gtcacaaaga gctaagagtt atccctagga caatctcatt agtgtagata catccattaa   600
tcttttatca gaggcaaacg taaagccgct ctttatgaca aaaataggtg acacaaaagt   660
gttatctgcc acatacataa cttcagaaat tacccaacac aagagaaaaa ataaaaaaaa   720 atcttttgc aagctccaaa tcttggaaac ttttttcact cttttgcagca ttgtactctt   780 gctcttttc caaccgatcc atgtcaccct caagcttcta cttgatctac acgaagctca   840
ccgtgcacac aaccatggcc acaaaaaccc tataaaaccc catccgatcg ccatcatctc   900
atcatcagtt cattaccaac aaacaaaaga ggaaaaaaaa catatacact tctagtgatt   960
gtctgattga tcatcaatct agaggcggcc gcatggctag caaggtcgtc ttcttcgcgg   1020
cggcgctcat ggcggccatg gtggccatct ccggc                             1055

<210> SEQ ID NO 8
<211> LENGTH: 976
<212> TYPE: DNA
<213> ORGANISM: Triticum sp.

<400> SEQUENCE: 8
ctgcaggcca gggaaagaca atggacatgc aaagaggtag gggcagggaa gaaacacttg    60
gagatcatag aagaacataa gaggttaaac ataggagggc ataatggaca attaaatcta   120
cattaattga actcatttgg gaagtaaaca aaatccatat tctggtgtaa atcaaactat   180
ttgacgcgga tttactaaga tcctatgtta attttagaca tgactggcca aaggtttcag   240
ttagttcatt tgtcacggaa aggtgttttc ataagtccaa aactctacca actttttgc    300
```

```
acgtcatagc atagatagat gttgtgagtc attggataga tatttgtagt cagcatggat      360
ttgtgttgcc tggaaatcca actaaatgac aagcaacaaa acctgaaatg ggctttagga      420
gagatggttt atcaatttac atgttccatg caggctacct tccactactc gacatggtta      480
gaagttttga gtgccgcata tttgcggaag caatggcact actcgacatg gttagaagtt      540
ttgagtgccg catatttgcg gaagcaatgg ctaacagata catattctgc caaaccccaa      600
gaaggataat cactcctctt agataaaaag aacagaccaa tgtacaaaca tccacacttc      660
tgcaaacaat acaccagaac taggattaag cccattacgt ggctttagca gaccgtccaa      720
aaatctgttt tgcaagcacc aattgctcct tacttatcca gcttcttttg tgttggcaaa      780 ctgcccttt ccaaccgatt tgtttcttc tcacgctttc ttcataggct aaactaacct      840
cggcgtgcac acaaccatgt cctgaacctt cacctcgtcc ctataaaagc ccatccaacc      900
ttacaatctc atcatcaccc acaacaccga gcaccccaat ctacagatca attcactgac      960
agttcactga tctaga                                                     976

<210> SEQ ID NO 9
<211> LENGTH: 1009
<212> TYPE: DNA
<213> ORGANISM: Oryza sp.

<400> SEQUENCE: 9
ctgcagtaat ggatacctag tagcaagcta gcttaaacaa atctaaattc caatctgttc       60
gtaaacgttt tctcgatcgc aattttgatc aaaactattg aaaacctcaa ttaaaccatt      120
caaaattttt aatatacca caagagcgt ccaaaccaaa tatgtaaata tggatgtcat       180
gataattgac ttatgacaat gtgattattt catcaagtct ttaaatcatt aattctagtt      240
gaaggtttat gttttcttat gctaaagggt tatgtttata taagaatatt aaagagcaaa      300
ttgcaataga tcaacacaac aaatttgaat gtttccagat gtgtaaaaat atccaaatta      360
attgttttaa aatagttta agaaggatct gatatgcaag tttgatagtt agtaaactgc      420
aaaagggctt attacatgga aaattcctta ttgaatatgt tcattgact ggtttatttt      480 acatgacaac aaagttacta gtatgtcaat aaaaaaatac aaggttactt gtcaattgta      540
ttgtgccaag taaagatgac aacaaacata caaatttatt tgttctttta tagaaacacc      600
taacttatca aggatagttg gccacgcaaa aatgacaaca tactttacaa ttgtatcatc      660
ataaagatct tatcaagtat aagaacttta tggtgacata aaaataatc acaagggcaa      720 gacacatact aaaagtatgg acagaaattt cttaacaaac tccatttgtt ttgtatccaa      780 agcataaga aatgagtcat ggctgagtca tgatatgtag ttcaatcttg caaaattgcc      840
tttttgttaa gtattgtttt aacactacaa gtcacatatt gtctatactt gcaacaaaca      900
ctattaccgt gtatcccaag tggcctttc attgctatat aaactagctt gatcggtctt      960
tcaactcaca tcaattagct taagtttcca ttagcaactg ctaatagct             1009

<210> SEQ ID NO 10
<211> LENGTH: 839
<212> TYPE: DNA
<213> ORGANISM: Oryza sp.

<400> SEQUENCE: 10
ctgcagtgta agtgtagctt cttatagctt agtgctttac tatcttcaca agcacatgct       60
atagtattgt tccaagatga aagaataatt catccttgct accaacttgc atgatattat      120
atttgtgaat atcctatctc ttggcttata atgaaatgtg ctgctgggtt attctgacca      180
```

-continued

```
tggtatttga gagcctttgt atagctgaaa ccaacgtata tcgagcatgg aacagagaac    240
aaaatgcaag gattttttta ttctggttca tgccctggat gggttaatat cgtgatcatc    300
aaaaaagata tgcataaaat taagtaata aatttgctca taagaaacca aaaccaaaag    360
cacatatgtc ctaaacaaac tgcattttgt ttgtcatgta gcaatacaag agataatata    420
tgacgtggtt atgacttatt cacttttgt gactccaaaa tgtagtaggt ctaactgatt    480
gtttaaagtg atgtcttact gtagaagttt catcccaaaa gcaatcacta aagcaacaca    540
cacgtatagt ccaccttcac gtaattcttt gtggaagata acaagaaggc tcactgaaaa    600
ataaaagcaa agaaaaggat atcaaacaga ccattgtgca tcccattgat ccttgtatgt    660
ctatttatct atcctccttt tgtgtacctt acttctatct agtgagtcac ttcatatgtg    720
gacattaaca aactctatct taacatctag tcgatcacta ctttacttca ctataaaagg    780
accaacatat atcatccatt tctcacaaaa gcattgagtt cagtcccaca aaatctaga    839
```

<210> SEQ ID NO 11
<211> LENGTH: 1302
<212> TYPE: DNA
<213> ORGANISM: Oryza sp.

<400> SEQUENCE: 11

```
ctgcagagat atggattttc taagattaat tgattctctg tctaaagaaa aaagtatta    60 ttgaattaaa tggaaaaaga aaaggaaaa aggggatggc ttctgctttt tgggctgaag   120
gcggcgtgtg gccagcgtgc tgcgtgcgga cagcgagcga acacgacg gagcagctac   180 gacgaacggg ggaccgagtg gaccggacga ggatgtggcc taggacgagt gcacaaggct   240
agtggactcg gtccccgcgc ggtatcccga gtggtccact gtctgcaaac acgattcaca   300
tagagcgggc agacgcggga gccgtcctag gtgcaccgga agcaaatccg tcgcctgggt   360
ggatttgagt gacacggccc acgtgtagcc tcacagctct ccgtggtcag atgtgtaaaa   420
ttatcataat atgtgttttt caaatagtta aataatatat ataggcaagt tatatgggtc   480
aataagcagt aaaaaggctt atgacatggt aaaattactt acaccaatat gccttactgt   540
ctgatatatt ttacatgaca acaaagttac aagtacgtca tttaaaaata caagttactt   600
atcaattgta gtgtatcaag taaatgacaa caaacctaca aatttgctat tttgaaggaa   660
cacttaaaaa aatcaatagg caagttatat agtcaataaa ctgcaagaag cttatgaca   720 tggaaaaatt acatacacca atatgcttta ttgtccggta tattttacaa gacaacaaag   780
ttataagtat gtcatttaaa aatacaagtt acttatcaat tgtcaagtaa atgaaaacaa   840
acctacaaat ttgttatttt gaaggaacac ctaaattatc aaatatagct tgctacgcaa   900
aatgacaaca tgcttacaag ttattatcat cttaaagtta gactcatctt ctcaagcata   960
agagctttat ggtgcaaaaa caaatataat gacaaggcaa agatacatac atattaagag  1020
tatggacaga catttcttta acaaactcca tttgtattac tccaaaagca ccagaagttt  1080
gtcatggctg agtcatgaaa tgtatagttc aatcttgcaa agttgccttt ccttttgtac  1140
tgtgttttaa cactacaagc catatattgt ctgtacgtgc aacaaactat atcaccatgt  1200
atcccaagat gcttttttat tgctatataa actagcttgg tctgtctttg aactcacatc  1260
aattagctta agtttccata agcaagtaca aatagctcta ga                     1302
```

<210> SEQ ID NO 12
<211> LENGTH: 675
<212> TYPE: DNA

<213> ORGANISM: Oryza sp.

<400> SEQUENCE: 12

```
ctgcagcatc ggcttaggtg tagcaacacg actttattat tattattatt attattatta      60
ttattttaca aaatatataaa atagatcagt ccctcaccac aagtagagca agttggtgag    120
ttattgtaaa gttctacaaa gctaatttaa aagttattgc attaacttat ttcatattac    180
aaacaagagt gtcaatggaa caatgaaaac catatgacat actataattt tgtttttatt    240
attgaaatta taattcaa agagaataaa tccacatagc cgtaaagttc tacatgtggt     300
gcattaccaa aatatatata gcttacaaaa catgacaagc ttagtttgaa aaattgcaat    360
ccttatcaca ttgacacata aagtgagtga tgagtcataa tattattttt cttgctaccc    420
atcatgtata tatgatagcc acaaagttac tttgatgatg atatcaaaga acatttttag    480
gtgcacctaa cagaatatcc aaataatatg actcacttag atcataatag agcatcaagt    540
aaaactaaca ctctaaagca accgatggga aagcatctat aaatagacaa gcacaatgaa    600
aatcctcatc atccttcacc acaattcaaa tattatagtt gaagcatagt agtagaatcc    660
aacaacaatc tagag                                                     675
```

<210> SEQ ID NO 13
<211> LENGTH: 1098
<212> TYPE: DNA
<213> ORGANISM: Oryza sp.

<400> SEQUENCE: 13

```
ccaggcttca tcctaaccat tacaggcaag atgttgtatg aagaagggcg aacatgcaga      60
ttgttaaact gacacgtgat ggacaagaat gaccgattgg tgaccggtct gacaatggtc    120
atgtcgtcag cagacagcca tctcccacgt cgcgcctgct tccggtgaaa gtggaggtag    180
gtatgggccg tcccgtcaga aggtgattcg gatggcagcg atacaaatct ccgtccatta    240
atgaagagaa gtcaagttga agaaaggga gggagagatg gtgcatgtgg gatcccttg     300
ggatataaaa ggaggacctt gcccacttag aaaggagagg agaaagcaat cccagaagaa    360
tcggggctg actggcactt tgtagcttct tcatacgcga atccaccaaa acacaggagt    420
agggtattac gcttctcagc ggcccgaacc tgtatacatc gcccgtgtct tgtgtgtttc    480
cgctcttgcg aaccttccac agattgggag cttagaacct cacccagggc cccggccga    540
actggcaaag gggggcctgc gcggtctccc ggtgaggagc cccacgctcc gtcagttcta    600
aattacccga tgagaaaggg aggggggggg gggaaatctg ccttgtttat ttacgatcca    660
acggatttgg tcgacaccga tgaggtgtct taccagttac cacgagctag attatagtac    720
taattacttg aggattcggt tcctaatttt ttacccgatc gacttcgcca tggaaaattt    780
tttattcggg ggagaatatc caccctgttt cgctcctaat taagatagga attgttacga    840
ttagcaacct aattcagatc agaattgtta gttagcggcg ttggatccct cacctcatcc    900
catcccaatt cccaaaccca aactcctctt ccagtcgccg acccaaacac gcatccgccg    960
cctataaatc ccaccgcat cgagcctatc aagcccaaaa aaccacaaac caaacgaaga   1020
aggaaaaaaa aaggaggaaa agaaaagagg aggaaagcga agaggttgga gagagacgct   1080
cgtctccacg tcgccgcc                                                 1098
```

<210> SEQ ID NO 14
<211> LENGTH: 432
<212> TYPE: DNA
<213> ORGANISM: Hordeum sp.

```
<400> SEQUENCE: 14
cttcgagtgc cgccgattt gccagcaatg gctaacagac acatattctg ccaaaacccc      60
agaacaataa tcacttctcg tagatgaaga gaacagacca agatacaaac gtccacgctt     120
cagcaaacag taccccagaa ctaggattaa gccgattacg cggctttagc agaccgtcca    180
aaaaaactgt tttgcaaagc tccaattcct ccttgcttat ccaatttctt ttgtgttggc     240
aaactgcact tgtccaaccg attttgttct tcccgtgttt cttcttaggc taactaacac    300
agccgtgcac atagccatgg tccggaatct tcacctcgtc cctataaaag cccagccaat    360
ctccacaatc tcatcatcac cgagaacacc gagaaccaca aaactagaga tcaattcatt    420
gacagtccac cg                                                        432

<210> SEQ ID NO 15
<211> LENGTH: 60
<212> TYPE: DNA
<213> ORGANISM: Triticum sp.

<400> SEQUENCE: 15
atggctaagc gcctggtcct ctttgcggca gtagtcgtcg ccctcgtggc tctcaccgcc      60

<210> SEQ ID NO 16
<211> LENGTH: 72
<212> TYPE: DNA
<213> ORGANISM: Oryza sp.

<400> SEQUENCE: 16
atggcaacta ccatttctc tcgttttcct atatactttt gtgctatgct attatgccag      60
ggttctatgg cc                                                         72

<210> SEQ ID NO 17
<211> LENGTH: 85
<212> TYPE: DNA
<213> ORGANISM: Oryza sp.

<400> SEQUENCE: 17
atgtggacat taacaaactc tatcttaaca tctagtcgat cactacttta cttcactata      60
aaaggaccaa catatatcat ccatt                                           85

<210> SEQ ID NO 18
<211> LENGTH: 72
<212> TYPE: DNA
<213> ORGANISM: Oryza sp.

<400> SEQUENCE: 18
atggcgagtt ccgttttctc tcggttttct atatactttt gtgttcttct attatgccat      60
ggttctatgg cc                                                         72

<210> SEQ ID NO 19
<211> LENGTH: 69
<212> TYPE: DNA
<213> ORGANISM: Oryza sp.

<400> SEQUENCE: 19
atgaagatca ttttcgtatt tgctctcctt gctattgttg catgcaacgc ttctgcacgg      60
tttgatgct                                                             69

<210> SEQ ID NO 20
```

```
<211> LENGTH: 63
<212> TYPE: DNA
<213> ORGANISM: Oryza sp.

<400> SEQUENCE: 20
atggccgccc gcgccgccgc cgccgcgttc ctgctgctgc tcatcgtcgt tggtcaccgc    60
gcc                                                                  63

<210> SEQ ID NO 21
<211> LENGTH: 63
<212> TYPE: DNA
<213> ORGANISM: Hordeum sp.

<400> SEQUENCE: 21
atggctaagc ggctggtcct ctttgtggcg gtaatcgtcg ccctcgtggc tctcaccacc    60
gcc                                                                  63
```